United States Patent
Amrich et al.

(10) Patent No.: US 7,018,418 B2
(45) Date of Patent: Mar. 28, 2006

(54) TEXTURED SURFACE HAVING UNDERCUT MICRO RECESSES IN A SURFACE

(75) Inventors: Mark Amrich, Tyngsborough, MA (US); Jonathan L. Rolfe, North Easton, MA (US); Joseph Buturlia, Boxford, MA (US); Robert F. Lynch, Newburyport, MA (US)

(73) Assignee: Tecomet, Inc., Wilmington, MA (US)

( * ) Notice: Subject to any disclaimer, the term of this patent is extended or adjusted under 35 U.S.C. 154(b) by 0 days.

(21) Appl. No.: 10/202,575

(22) Filed: Jul. 24, 2002

(65) Prior Publication Data

US 2003/0065401 A1    Apr. 3, 2003

Related U.S. Application Data

(63) Continuation-in-part of application No. 10/021,616, filed on Dec. 12, 2001, now Pat. No. 6,620,332, which is a continuation-in-part of application No. 09/976,722, filed on Oct. 12, 2001, now Pat. No. 6,599,322.

(60) Provisional application No. 60/391,957, filed on Jun. 25, 2002, provisional application No. 60/388,033, filed on Jun. 12, 2002, provisional application No. 60/356,459, filed on Feb. 11, 2002, provisional application No. 60/340,286, filed on Dec. 12, 2001, provisional application No. 60/309,923, filed on Aug. 3, 2001, provisional application No. 60/291,002, filed on May 15, 2001, provisional application No. 60/264,084, filed on Jan. 25, 2001.

(51) Int. Cl.
*A61F 2/28* (2006.01)
*A61F 2/02* (2006.01)

(52) U.S. Cl. .................. 623/23.5; 623/23.74

(58) Field of Classification Search ............... 623/1.39, 623/1.4, 22.27, 23.29–23.31, 23.5, 23.55, 623/23.74, 17.11, 17.16, 17, 23.72; 428/141
See application file for complete search history.

(56) References Cited

U.S. PATENT DOCUMENTS

| | | |
|---|---|---|
| 852,873 A | 5/1907 | Davidson |
| 3,045,321 A | 7/1962 | McDermott |
| 3,359,192 A | 12/1967 | Heinrich et al. |
| 3,558,310 A | 1/1971 | Mayaud |
| 3,605,123 A | 9/1971 | Hahn |
| 3,679,500 A | 7/1972 | Kubo et al. |
| 3,905,080 A | 9/1975 | Bond |
| 4,033,831 A | 7/1977 | Bakewell |
| 4,069,085 A | 1/1978 | Buysman et al. |

(Continued)

FOREIGN PATENT DOCUMENTS

CN    1186874 A    7/1998

(Continued)

OTHER PUBLICATIONS

International Search Report, Application Serial No. PCT/US02/13618, Oct. 3, 2002.

(Continued)

*Primary Examiner*—Corrine McDermott
*Assistant Examiner*—Cheryl Miller
(74) *Attorney, Agent, or Firm*—Morgan, Lewis & Bockius, LLP

(57) ABSTRACT

Textured surface having micro recesses such that the outer surface overhangs the micro recesses. Embodiments of the textured surface include sharp edges for promoting bone deposition and growth within the micro recesses, protrusions of varying depth from the surface that include overhangs, and micro recesses that are at least partially defined by complex ellipsoids.

25 Claims, 30 Drawing Sheets

U.S. PATENT DOCUMENTS

| | | | |
|---|---|---|---|
| 4,272,855 | A | 6/1981 | Frey |
| 4,284,468 | A | 8/1981 | Stearns |
| 4,330,891 | A | 5/1982 | Branemark et al. |
| 4,355,428 | A | 10/1982 | Deloison et al. |
| 4,422,465 | A | 12/1983 | Haga |
| 4,456,500 | A | 6/1984 | Ibata |
| 4,470,872 | A | 9/1984 | Sudo et al. |
| 4,528,070 | A | 7/1985 | Gamblin |
| 4,608,052 | A | 8/1986 | Van Kampen et al. |
| 4,632,726 | A | 12/1986 | Thoms |
| 4,634,603 | A | 1/1987 | Gruss et al. |
| 4,644,942 | A | 2/1987 | Sump |
| 4,662,984 | A | 5/1987 | Ohtake et al. |
| 4,664,668 | A | 5/1987 | Beck et al. |
| 4,673,409 | A | 6/1987 | Van Kampen |
| 4,714,470 | A | 12/1987 | Webb, Jr. et al. |
| 4,725,334 | A | 2/1988 | Brimm |
| 4,752,294 | A | 6/1988 | Lundgren |
| 4,803,098 | A | 2/1989 | Henri et al. |
| 4,834,756 | A | 5/1989 | Kenna |
| 4,836,837 | A | 6/1989 | Rapp |
| 4,836,884 | A | 6/1989 | McAuslan |
| 4,846,839 | A | 7/1989 | Noiles |
| 4,851,008 | A | 7/1989 | Johnson |
| 4,863,474 | A | 9/1989 | Brown et al. |
| 4,863,475 | A | 9/1989 | Andersen et al. |
| 4,865,603 | A | 9/1989 | Noiles |
| 4,871,366 | A | 10/1989 | von Recum et al. |
| 4,900,387 | A | 2/1990 | Johnson |
| H788 | H | 6/1990 | Schneider, Jr. |
| 4,944,763 | A | 7/1990 | Willert et al. |
| 4,955,909 | A | 9/1990 | Ersek et al. |
| 4,959,275 | A | 9/1990 | Iguchi et al. |
| 4,960,381 | A | 10/1990 | Niznick |
| 4,969,904 | A | 11/1990 | Koch et al. |
| 4,976,738 | A | 12/1990 | Frey et al. |
| 4,978,358 | A | 12/1990 | Bobyn |
| 4,989,304 | A | 2/1991 | Sonefors |
| 5,002,572 | A | 3/1991 | Picha |
| 5,002,575 | A | 3/1991 | Johnson |
| 5,002,580 | A | 3/1991 | Noble et al. |
| 5,007,931 | A | 4/1991 | Smith |
| 5,011,494 | A | 4/1991 | von Recum et al. |
| 5,100,508 | A | 3/1992 | Yoshida et al. |
| 5,108,434 | A | 4/1992 | Ahrens et al. |
| 5,139,528 | A | 8/1992 | Koch et al. |
| 5,207,709 | A | 5/1993 | Picha |
| 5,219,361 | A | 6/1993 | von Recum et al. |
| 5,222,983 | A | 6/1993 | Schmitz et al. |
| 5,236,459 | A | 8/1993 | Koch et al. |
| 5,246,530 | A | 9/1993 | Bugle et al. |
| 5,258,098 | A | 11/1993 | Wagner et al. |
| 5,268,068 | A | 12/1993 | Cowell et al. |
| 5,271,736 | A | 12/1993 | Picha |
| 5,298,115 | A | 3/1994 | Leonard |
| 5,307,594 | A | 5/1994 | Panchison |
| 5,358,533 | A | 10/1994 | Noiles et al. |
| 5,456,723 | A | 10/1995 | Steinemann et al. |
| 5,484,074 | A | 1/1996 | Deibler et al. |
| 5,507,815 | A | 4/1996 | Wagner et al. |
| 5,526,950 | A | 6/1996 | Tago et al. |
| 5,549,704 | A | 8/1996 | Sutter |
| 5,553,476 | A * | 9/1996 | Oehy et al. ............... 72/325 |
| 5,571,017 | A | 11/1996 | Niznick |
| 5,593,409 | A * | 1/1997 | Michelson ............... 606/61 |
| 5,603,338 | A | 2/1997 | Beaty |
| 5,606,589 | A | 2/1997 | Pellegrino et al. |
| 5,607,480 | A | 3/1997 | Beaty |
| 5,639,237 | A | 6/1997 | Fontenot |
| 5,645,593 | A | 7/1997 | Woods et al. |
| 5,645,740 | A | 7/1997 | Naiman et al. |
| 5,658,334 | A | 8/1997 | Caldarise et al. |
| 5,665,118 | A | 9/1997 | LaSalle et al. |
| 5,665,121 | A | 9/1997 | Gie et al. |
| 5,676,850 | A | 10/1997 | Reed et al. |
| 5,709,804 | A | 1/1998 | Makita et al. |
| 5,713,410 | A | 2/1998 | LaSalle et al. |
| 5,716,412 | A | 2/1998 | DeCarlo, Jr. et al. |
| 5,728,159 | A | 3/1998 | Stroever et al. |
| 5,730,887 | A | 3/1998 | Simpson et al. |
| 5,814,235 | A | 9/1998 | Pellegrino et al. |
| 5,826,586 | A | 10/1998 | Mishra et al. |
| 5,830,373 | A | 11/1998 | Ohtake et al. |
| 5,843,250 | A | 12/1998 | Bone et al. |
| 5,853,561 | A | 12/1998 | Banks |
| 5,876,457 | A * | 3/1999 | Picha et al. ............... 623/17.11 |
| 5,897,592 | A | 4/1999 | Caldarise et al. |
| 5,910,173 | A | 6/1999 | DeCarlo, Jr. et al. |
| 5,922,029 | A | 7/1999 | Wagner et al. |
| 5,958,314 | A * | 9/1999 | Draenert ............... 264/42 |
| 5,965,006 | A | 10/1999 | Baege et al. |
| 5,975,903 | A | 11/1999 | Shoher et al. |
| 6,005,164 | A | 12/1999 | Johansson et al. |
| 6,008,430 | A | 12/1999 | White |
| 6,008,431 | A | 12/1999 | Caldarise et al. |
| 6,008,432 | A | 12/1999 | Taylor |
| 6,010,336 | A | 1/2000 | Shimotoso et al. |
| 6,069,295 | A | 5/2000 | Leitao |
| 6,095,817 | A | 8/2000 | Wagner et al. |
| 6,106,558 | A | 8/2000 | Picha |
| 6,149,688 | A | 11/2000 | Brosnahan et al. |
| 6,149,689 | A | 11/2000 | Grundei |
| 6,171,344 | B1 | 1/2001 | Atala |
| 6,193,756 | B1 * | 2/2001 | Studer et al. ............ 623/17.15 |
| 6,193,762 | B1 | 2/2001 | Wagner et al. |
| 6,200,346 | B1 | 3/2001 | Baege et al. |
| 6,217,333 | B1 | 4/2001 | Ercoli |
| 6,217,615 | B1 | 4/2001 | Sioshansi et al. |
| 6,221,109 | B1 | 4/2001 | Geistlich et al. |
| 6,235,125 | B1 | 5/2001 | Cercone et al. |
| 6,235,638 | B1 | 5/2001 | Huang et al. |
| 6,261,322 | B1 | 7/2001 | Despres, III et al. |
| 6,270,530 | B1 | 8/2001 | Eldridge et al. |
| 6,277,150 | B1 | 8/2001 | Crawley et al. |
| 6,280,477 | B1 * | 8/2001 | Mastrorio et al. ....... 623/23.48 |
| 6,302,913 | B1 * | 10/2001 | Ripamonti et al. ...... 623/16.11 |
| 6,312,612 | B1 | 11/2001 | Sherman et al. |
| 6,315,798 | B1 | 11/2001 | Ashby et al. |
| 6,344,061 | B1 | 2/2002 | Leitao et al. |
| 6,419,491 | B1 * | 7/2002 | Ricci et al. ............... 433/173 |
| 6,436,139 | B1 * | 8/2002 | Shapiro et al. .......... 623/17.11 |
| 6,485,521 | B1 * | 11/2002 | Say et al. ............... 623/23.55 |
| 6,811,837 | B1 * | 11/2004 | Iwasa et al. ............ 428/32.17 |
| 2001/0039454 | A1 | 11/2001 | Ricci et al. |
| 2003/0006534 | A1 * | 1/2003 | Taboas et al. ............ 264/401 |
| 2003/0125739 | A1 * | 7/2003 | Bagga et al. ............ 606/61 |
| 2003/0186828 | A1 * | 10/2003 | Holderbaum et al. ..... 510/224 |
| 2004/0002759 | A1 * | 1/2004 | Ferree ............... 623/17.11 |

FOREIGN PATENT DOCUMENTS

| | | |
|---|---|---|
| EP | 0 850 702 A2 | 1/1998 |
| GB | 2206614 A | 1/1989 |
| JP | 06125978 A | 5/1994 |

OTHER PUBLICATIONS

International Search Report, Application Serial No. PCT/US02/02066, Oct. 3, 2002.

Partial European Search Report, Application Serial No. 02001558, Apr. 16, 2002.

International Search Report, Application Serial No. PCT/US02/39743, Apr. 21, 2003.

* cited by examiner

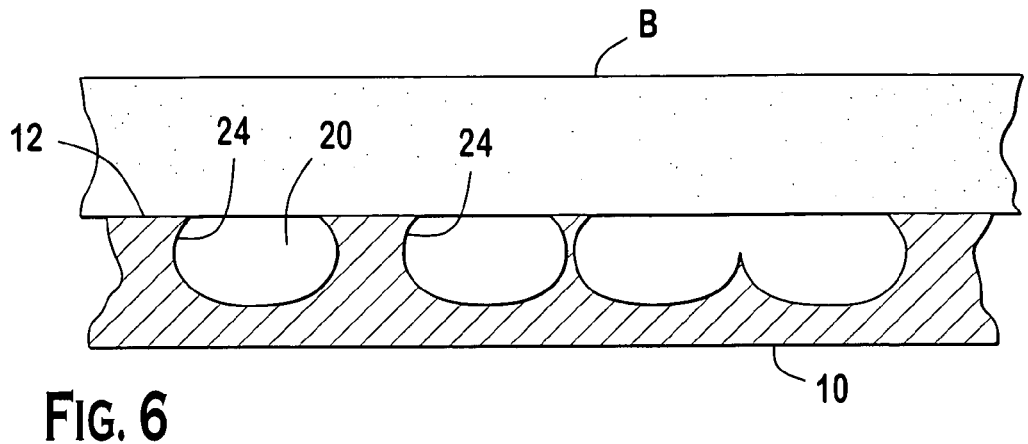
FIG. 6
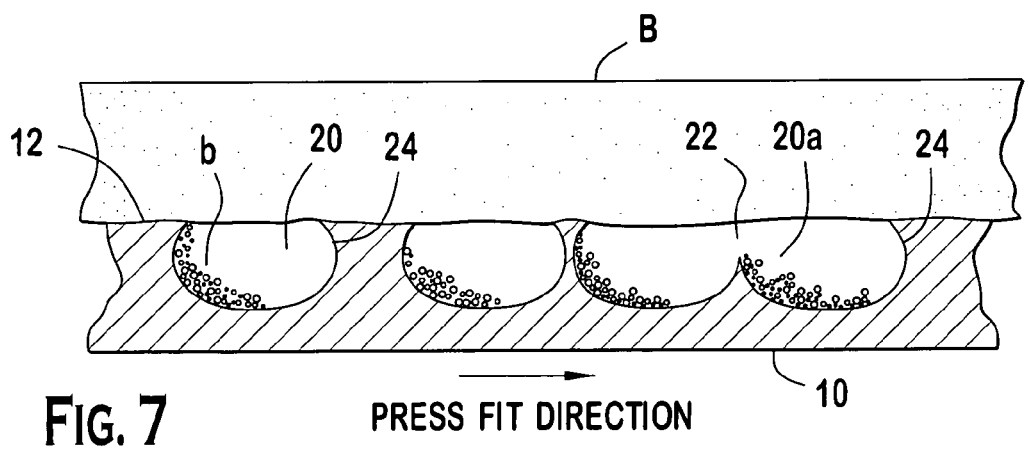
FIG. 7    PRESS FIT DIRECTION →
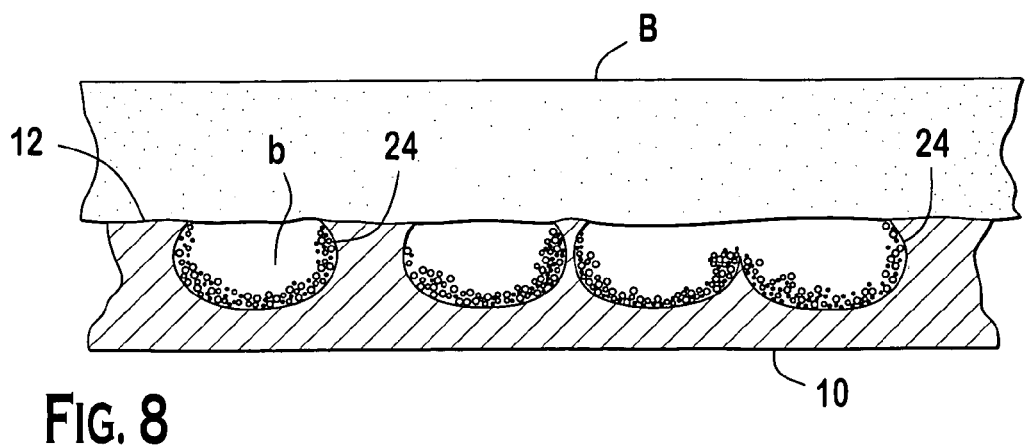
FIG. 8

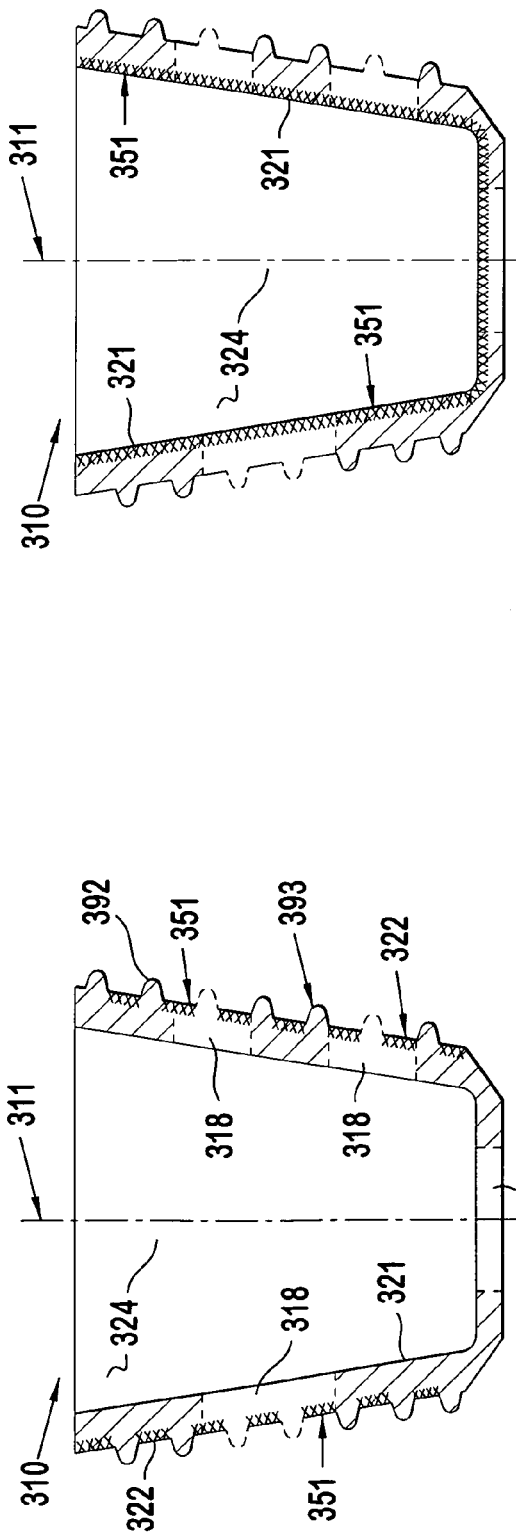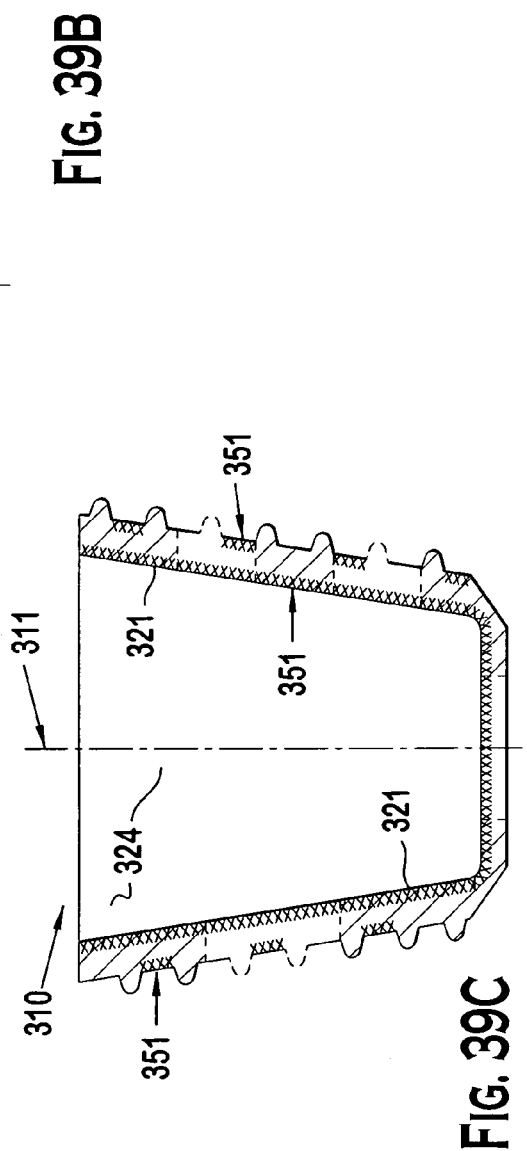

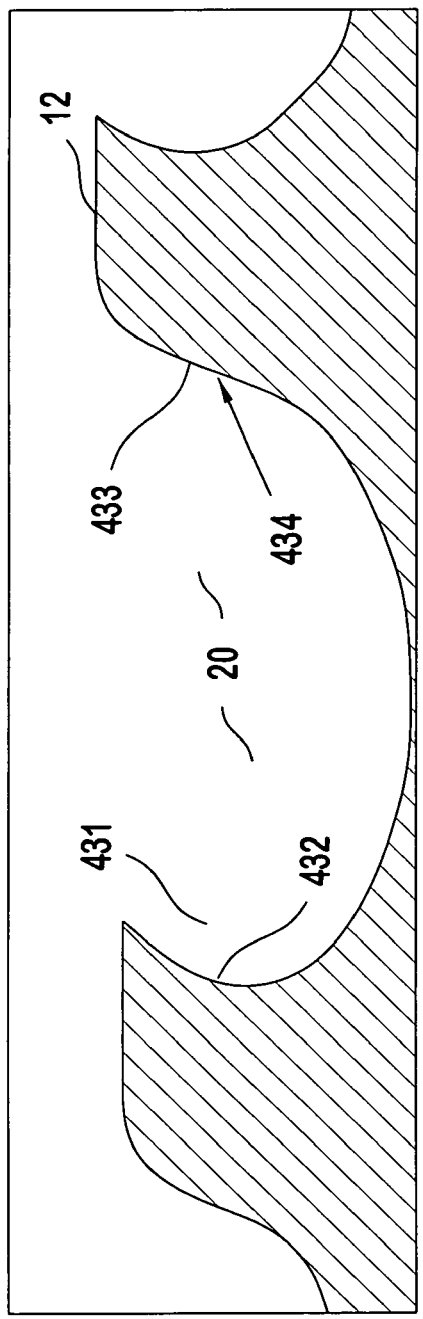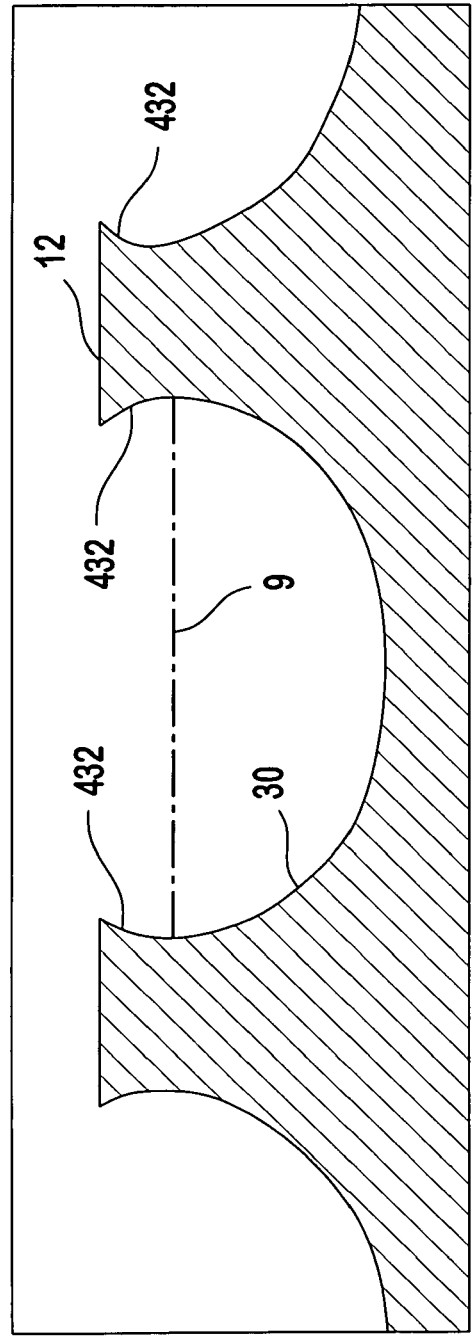
FIG. 42A
FIG. 42B

TEXTURED SURFACE HAVING UNDERCUT MICRO RECESSES IN A SURFACE

CROSS-REFERENCE TO RELATED APPLICATIONS

This application is a continuation-in part of U.S. application Ser. No. 09/976,722 filed Oct. 12, 2001, now U.S. Pat. No. 6,599,322 which claims the benefit of U.S. Provisional Application No. 60/264,084 filed, Jan. 25, 2001, and U.S. Provisional Application No. 60/309,923, filed Aug. 3, 2001. This application is also a continuation-in-part of U.S. application Ser. No. 10/021,616, filed Dec. 12, 2001, now U.S. Pat. No. 6,620,332 which claims benefit of U.S. Provisional Application 60/291,022, filed May 15, 2001. This application, furthermore, claims the benefit of priority of U.S. Provisional Application No. 60/340,286, filed Dec. 12, 2001, U.S. Provisional Application No. 60/356,459, filed Feb. 11, 2002, U.S. Provisional Application No. 60/388,033, filed Jun. 12, 2002, and U.S. Provisional Application No. 60/391,957, filed Jun. 25, 2002.

BACKGROUND OF THE INVENTION

1. Field of the Invention

The invention relates to the production of textured surfaces for medical, industrial, and commercial applications and is directed more particularly to surfaces having undercut micro recesses.

2. Description of the Prior Art

It is known to use textured surfaces on surgical implants for the purpose of encouraging bone adhesion and thus stabilizing the location of the implant relative to the bone. For example, in an artificial hip, including a femoral sub-assembly for positioning in a patient's femur, and an acetabular sub-assembly for positioning in the patient's acetabulum, the femoral sub-assembly includes an artificial stem which is typically provided with a textured surface, and the acetabular sub-assembly includes an acetabular cup which is typically provided with a textured surface, the textured surfaces being provided to promote bone in-growth.

The desirability of roughened, textured, bone-engaging surfaces to assure stable positioning of surgical implants has been recognized in U.S. Pat. No. 5,298,115, issued Mar. 29, 1994, in the name of Ian Leonard, U.S. Pat. No. 5,456,723, issued Oct. 10, 1995, in the name of Samuel G. Steinemann, U.S. Pat. No., 5,603,338, issued Feb. 18, 1997, in the name of Keith D. Beaty, U.S. Pat. No. 5,853,561, issued Dec. 29, 1998, in the name of Bruce A. Banks, and U.S. Pat. No. 5,965,006, issued Oct. 12, 1999, in the names of Roland Baege et al.

To produce such textured surfaces, one known method is to provide a mass of titanium spheres vacuum fused onto the datum surface of the implant. This method is described in U.S. Pat. No. 4,834,756, issued May 30, 1989, to Robert V. Kenna. In a similar procedure, described in U.S. Pat. No. 4,644,942, issued Feb. 24, 1987 to Kenneth R. Sump, an extractable component and titanium spheres are densified as a coating, which is fused onto a datum surface of the implant, and the extractable component subsequently is extracted. While an improvement over untreated metal, questions have arisen over the longevity of usefulness of the implanted devices utilizing such surfaces. It is questionable whether there is substantial genuine adhesion. It is believed that the voids formed by the spheres are not sufficient for long-term nourishment of ingrowing tissue and/or bone. Further, there have been failures of prosthetics treated in this manner because of the fusing process adversely affecting metallurgical properties. of the implant material, and because of difficulties in removing manufacturing contaminants, such as cutting oils, from the fused sphere network. Still further, the original datum surface, which can be accurately determined, is lost by the application of the coating spheres.

The formation of perforated thin metallic sheets or plates by means of chemical milling and/or photo-chemical etching techniques has been described in U.S. Pat. No. 3,359,192, issued Dec. 19, 1967, in the names of Hans-Joachim Heinrich et al., U.S. Pat. No. 5,606,589, issued Feb. 25, 1997, in the names of Anthony J. Pellegrino et al., and U.S. Pat. No. 5,814,235, issued Sep. 29, 1998, in the names of Anthony J. Pellegrino et al. The processes therein described have been found lacking in precise control over the degree and extent of roughness or texturing.

SUMMARY OF THE PREFERRED EMBODIMENTS

A preferred embodiment of the invention is a textured surface which is adapted to interlock with an adjacent body and method of producing a textured surface.

A further embodiment is to provide a texture having an undercut micro recesses in a surface of a body and method of producing a textured surface.

A still further embodiment provides recesses in a desired pattern which is measurable and predictable, and which can be duplicated and repeated precisely in any selected number of surfaces and method of producing a textured surface.

A still further embodiment is a surgical implant device wherein the material of the device retains its metallurgical properties throughout production and method of producing a textured surface.

A still further embodiment is a surgical implant, with a textured surface that promotes the in-growth of tissue and/or bone to securely interconnect the implant and the tissue and/or bone and method of producing a textured surface.

A still further object is to provide an implant with surfaces that include undercut and interconnecting recesses which promote and facilitate ingrowth of bone and which, upon implantation, facilitate a "scratch fit" with bone, to stabilize the position of the surface on the bone and to initiate an interconnection process between the implant and the bone. The "scratch fit" is accomplished by the textured surface scraping bone from the implant site during a press fit implantation, thereby producing autografted bone in the voids of the textured surface.

A still further embodiment is a surgical implant for attachment to tissue (e.g., bone).

A still further embodiment is a surgical implant for attachment to bone.

A still further embodiment is a surgical implant facilitating bone harvesting and seeding of the surgical implant with particulate bone matter during attachment of the implant to the bone.

A still further embodiment is a surgical implant which exhibits a precise fit with a bone implant site, to reduce micro-motion between the implant and the bone site.

A still further embodiment of the invention is to provide a surgical implant having undercut micro recesses with sharply defined edges in a bone-engaging surface thereof.

Yet another embodiment of the invention is the provision of an article, having a surface that includes a multiplicity of undercut microrecesses in the surface, such that the article thereby exhibits a greater fractal area at a level below the surface than is exhibited at the surface, the article produced by a method comprising the steps of applying a maskant layer to substantially an entirety of the article surface, removing the maskant layer in selected loci to expose underlying portions of the article surface in a selected, predictable, and reproducible pattern, applying an etchant to the exposed underlying surface portions for a time sufficient to etch the exposed surface portions and to enable the etchant to etch beneath remaining portions of the maskant layer and produce a multiplicity of undercut recesses, and removing the remaining maskant layer portions to provide the article surface in exposed condition with the multiplicity of recesses undercut and comprising interconnected recesses, to provide an engineered pattern of the recesses.

There is, furthermore, an article having a multiplicity of undercut micro recesses in a surface thereof, the recesses being in a selected pattern which can be repeated in any selected number of surfaces and produced by a method having the steps of: applying a maskant layer to substantially an entirety of a selected surface of the article; removing the maskant layer by computer-directed laser ablation in programmed loci to expose underlying portions of the surface of the article in a programmed pattern; applying an etchant to the exposed underlying surface portions for a time sufficient to etch the exposed surface portions and to enable the etchant to etch beneath remaining portions of the maskant layer and produce the multiplicity of undercut recesses; and removing the remaining maskant layer to provide the selected surface in exposed condition with the multiplicity of undercut recesses therein.

In accordance with a still another embodiment of the invention, there is provided a surgical implant having facility for stimulating ingrowth of bone upon attachment of the implant to a bone that is produced by a method that includes the steps of: providing a rigid article; applying a maskant layer to substantially an entirety of a datum surface of the article; removing portions of the maskant layer in selected loci to expose underlying portions of the surface of the article; applying an etchant to the exposed underlying surface portions for a time sufficient to etch the exposed surface portions and to enable the etchant to etch beneath remaining portions of the maskant layer and produce a multiplicity of undercut recesses having sharp edges at their intersections with the datum surface; and removing the remaining portions of the maskant layer to provide the datum surface in exposed condition with the sharp edges for shaving particulate matter from the bone, and with the recesses for receiving and retaining the bone particulate matter for stimulating ingrowth of bone.

In accordance with a still further embodiment of the invention, there is provided a textured surface in a surgical implant produced by a method that includes the steps of: applying a maskant layer to substantially an entirety of a datum surface of the implant; removing portions of the maskant layer in selected loci to expose underlying portions of the datum surface of the implant; applying an etchant to the exposed underlying datum surface portions for a time sufficient to etch the exposed surface portions and to enable the etchant to etch beneath remaining portions of the maskant layer and produce a multiplicity of undercut recesses having sharp edges at their intersections with the datum surface; and removing the remaining portions of the maskant layer to provide the datum surface in exposed condition with the sharp edges for shaving particulate matter from the bone, and with the recesses for receiving and retaining the bone particulate matter for stimulating in-growth of bone.

In accordance with a still further embodiment of the invention, there is provided a surgical implant that is attached to a bone, in accordance with a method comprising the steps of: providing a surgical implant having a datum surface, a multiplicity of micro recesses in the datum surface, and bone milling structure on the datum surface; pressing the datum surface against a surface of the bone; and urging the implant along the bone surface to mill particulate bone matter from the bone, wherein the recesses receive and retain the particulate bone matter to stimulate ingrowth of the bone into the datum surface.

In accordance with a still further embodiment of the invention, there is provided a surgical implant having a datum surface and a multiplicity of undercut microrecesses in the datum surface, such that the implant exhibits a greater fractal area at the level below the datum surface than is exhibited at the datum surface, intersections of the datum surface and the recesses defining sharp edges; pressing the datum surface against a surface of the bone, and urging the implant along the bone surface, to cause the sharp edges to shave particulate bone matter from the bone, wherein the recesses receive and retain the particulate bone matter to stimulate ingrowth of the bone to attach the surgical implant to the bone.

In accordance with a still further embodiment of the invention, there is provided a method for bone harvesting and seeding of a surgical implant with particulate bone matter during attachment of the implant to the bone, the method comprising the steps of providing a surgical implant having a surface for engagement with a bone surface, the implant having a multiplicity of undercut micro recesses and bone milling structure in the surface thereof, wherein moving the implant along the bone, such that the milling structure dislocates particulate bone matter from the bone, the bone matter falling into the micro recesses and retained thereby to stimulate ingrowth of the bone into the undercut recesses harvests the bone and seeds the surgical implant with particulate bone matter during attachment of the implant to the bone.

In accordance with a still further embodiment of the invention, there is a surgical implant having generally opposed datum surfaces spaced from each other by a predetermined distance, each of the datum surfaces being adapted to interlock with a bone surface that is made by a process comprising the steps of providing an article having first and second datum surface portions adapted to respectively engage first and second bone surfaces, the datum surface portions being spaced from each other by the predetermined distance which is substantially equal to a distance between the first and second bone surfaces; applying a maskant layer to substantially an entirety of each of the datum surfaces; removing the maskant layers in selected loci to expose underlying portions of the datum surfaces in a selected pattern; applying an etchant to the exposed underlying datum surface portions for a time sufficient to etch the exposed portions of the datum surfaces and to enable the etchant to etch beneath the remaining maskant layers and produce undercut recesses; and removing the remaining maskant to provide the opposed datum surfaces in exposed condition with the multiplicity of undercut recesses and devoid of structure protruding therefrom.

In accordance with a still further embodiment of the invention, there is provided a surgical implant comprising an article having a datum surface for abutting engagement with a bone, and a multiplicity of undercut micro recesses in the datum surface, such that the body exhibits a greater fractal area at a level below the surface than is exhibited at the surface. Intersections of the recesses and the datum surface define sharp edges adapted to cut the bone and produce bone particulates. The recesses are adapted to receive and retain the bone particulates cut from the bone by the edges, to stimulate ingrowth of the bone into the recesses.

For all objects of the invention that describe a device or a structure, the invention includes a method for producing the described devices or structures.

The above and other embodiments of the invention, including various novel details of components and method steps, will now be more particularly described with reference to the accompanying drawings and pointed out in the claims. It will be understood that the particular methods and devices embodying the invention are shown and described by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings:

FIGS. 6–10 are progressive diagrammatic sectional views showing positioning of the article adjacent a bone and interconnection of the article and the bone;

FIGS. 39A–39C are diagrammatic cross-sections illustrating textured implants;

FIG. 42A is a diagrammatic cross-sectional illustration of an implant having a directionally impinged textured surface; and FIG. 42B is a diagrammatic cross-sectional illustration of an implant having a non-directionally impinged textured surface.

DESCRIPTION OF THE PREFERRED EMBODIMENTS

Figure 1:
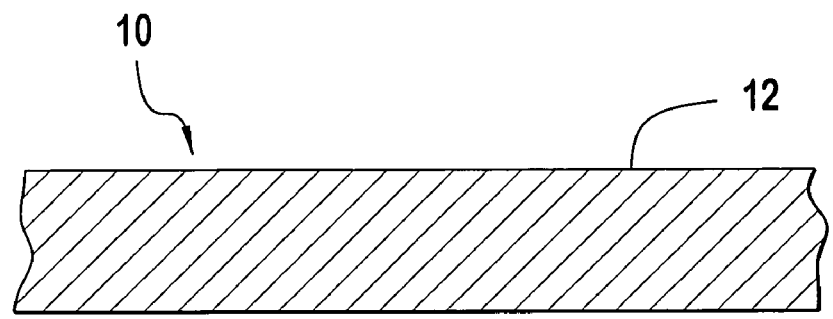
FIG. 1 is a diagrammatic sectional view of an article having a surface in which it is desired to provide a multiplicity of undercut micro recesses.

Undercutting occurs, for example, when the chemical etchant removes metal beyond the boundary of a maskant, or resist layer. Often, such undercutting limits the fine resolution needed for many processes, such as the production of electronic devices, rotogravure plates, and other fine parts. However, predetermined and controlled undercutting may be exploited and utilized to produce useful and novel three-dimensional geometries by allowing the undercutting effect to expand deeper regions of a chemically applied pattern, so that the resulting treatment layer is an engineered pattern of undercut recesses. This provides sharp geometries when desired, and produces a higher void volume and larger fractal dimensions than are obtainable by other methods. Further, it permits retention of a predetermined area of original surface to afford an engineered and repeatable "datum surface," or surface intended to abut another body to which the undercut surface will be attached. The metal of the complex pattern is identical and contiguous with the base metal of the treated body, because it is generated in the body, and not later applied, such as the fused metal spheres mentioned hereinabove.

While the methods and products described herein are described in terms of producing textured metal surfaces, and while it is expected that the method will find substantial utility in metal bodies, and while the method produces deeply textured surfaces in metals, such as titanium, zirconium, stainless steel and alloys thereof, tantalum, refractory metals, metal carbides, oxidized zirconium and cobalt/chromium, it will be appreciated that the method is readily adapted for use with bodies of other materials including ferrous and non-ferrous metals, and alloys thereof, ceramics, plastics and glass, and composites of metals, ceramics, plastics, and glass or any other material.

Application of the present invention is particularly useful in materials that are susceptible to so-called "nick-bend failures" or "notch failures." An example of a notch failure is crack propagation in metal surfaces. Such propagation is known to occur, for example, in materials having an applied surface texture. An example of a testing method for the measurement of creep crack growth rates in metals is provided in ASTM Standard E1457-00, which is herein incorporated by reference in its entirety.

One material that is particularly suited for implant applications is titanium. The susceptibility of titanium to crack propagation is well documented. Annealing is one method to relieve strain from a material surface such as titanium. Annealing, however, can have other deleterious effects on metals (e.g., increased softness). Another documented method for mitigating nick-bend failures is to strain relieve the material by, for example, removing the "rind", "skin" or outer surface of the metal that has been strained. Examples of techniques for removing rind includes machining, grinding, laser welding or laser machining involving thermal shock and sudden phase changes. These techniques may be employed to expose the pristine metal beneath the surface. In some cases, however, removing the rind from a textured surface has the unwanted effect of removing a portion of the texture. For example, where lasers are used to machine a metal (e.g., applying a texture to a surface using laser etching techniques), there is created an area of increased strain where the laser acted upon the surface of the material. One technique for strain release of that affected area is to remove the surface of the material. Where laser machining was performed for the purpose of applying a texture, removing that affected area would, in some cases, reduce or eliminate the effectiveness of the texture.

The methods and products of the present invention avoid this problem. To the extent that the laser ablation of maskant has a deleterious effect on the material being treated, in one embodiment of the invention, those effects are minimized or eliminated during the etching process resulting in a strain-reduced/relieved textured surface. That is, the strained regions of the surface are etched-away to relieve the strain, without forming a non-strained region.

Furthermore, it has been found that strained metal (such as where a laser has been applied to a surface) tends to etch, corrode or dissolve faster than metal in its pristine state. In a preferred embodiment, the laser ablation of maskant (e.g., to expose the surface of the metal for later etching) increases localized strain on the surface of the metal, thereby focusing future etching to produce a precisely textured strain-relieved surface. Furthermore, it has been found that the strained areas etch somewhat more quickly thereby promoting the preferentially accelerated resolution of these strains.

In preferred embodiments, the textures described herein are useful in the medical, industrial, consumer product, computer, electrical, and mechanical fields. For example, in the medical field, textures are useful in orthopeadic implants (e.g., in artificial hips, knees, acetabular cups, ankles, shoulders, and interbody fusion devices); spinal implants (e.g., spinal fusion devices, articulating intravertebrae devices, and external spinal fixation devices); neurocranial and maxillofacial implants (e.g., fracture plates and mesh, scafolds, and bridges); dental implants (e.g., osseointegration posts); joint replacement implants, cemented and cementless applications, and any medically implanted device where there is a need for improved fixation. Such improved fixation is useful between metal to tissue (e.g., bone), metal to plastic, metal to adhesive, soft tissue to bone, ligament to bone, soft tissue to implant, positional stability of implant (e.g., rough surface to hold implant in place during a surgical procedure) and for providing increased vascular flow (e.g., textured surface provides space between the implant and bone to allow for greater vascular flow between bone and implant).

In other fields, textures have use in any component device in which a material requires a surface conditioning to promote adhesion or increase friction. Exemplary fields include aerospace (e.g., fusilage bonding and fasteners); automotive (e.g., brake shoes to brake pads), sports gloves (e.g., rock climbing, football and golf gloves), composites (e.g., golf club heads, and any other contact surfaces where increased grip is desired), and tool sharpening. Other applications in industry and manufacturing will be apparent for the textured pattern of the present invention, including cutting surfaces (e.g., rasps, dental drills, medical files, burrs and orthopeadic cutters). Further utility will be found where improved adhesion is desired (e.g., metal to metal adhesion, polymer to polymer adhesion, metal to polymer adhesion, and on layers of material that are laminated to one another).

Among the characteristic features of the present invention are engineered patterns (e.g., application specific custom patterns and textures, repetitive or random patterns, patterns created on complex geometries, with no metallurgical changes in material, a chemically pure resulting surface, and a pattern that is integral with the parent material (e.g., not a coating). Application of these features achieves exemplary benefits such as: precise control of micropore size, accurate maintenance of a percentage of original surface; reduction of micromotion, and/or retention of bone chips shaved from undercut edges in texture pockets. Referring to FIG. 1, it will be seen that there first is provided an article 10 of one of the above-mentioned materials, or a material similar thereto. The article 10 is provided with a datum surface 12 in which it is desired to provide a multiplicity of undercut recesses.

Figure 2:
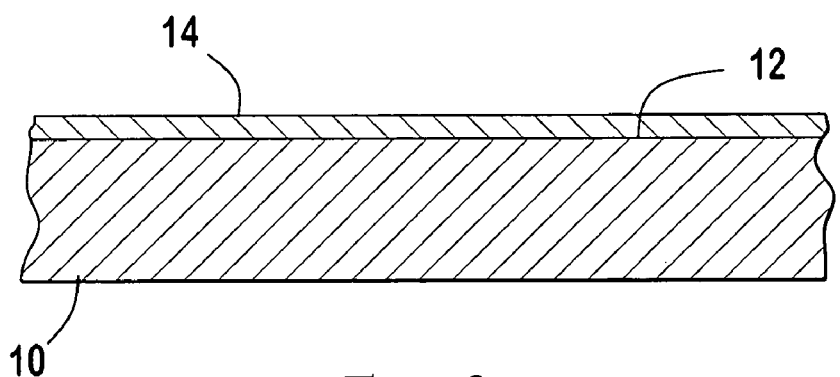
FIG. 2 depicts the article of FIG. 1 with a layer of maskant material deposited on the aforesaid surface.
Figure 3:
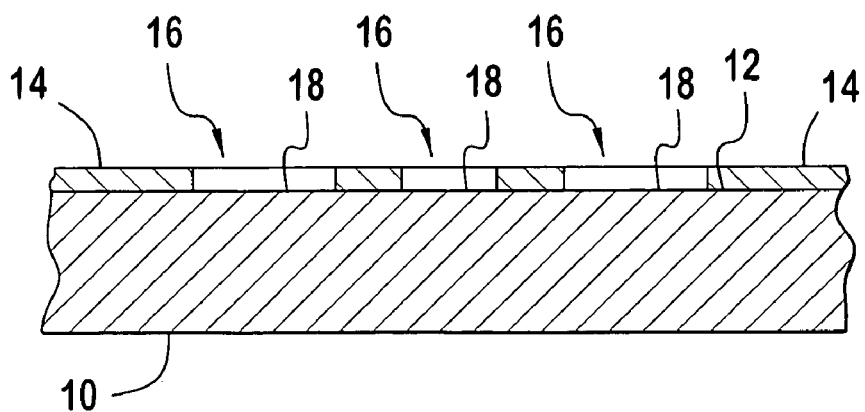
FIG. 3 depicts the article and maskant layer of FIG. 2 with the maskant layer in part removed.

As shown in FIG. 2, a layer 14 of maskant material is deposited on substantially the entirety of the surface 12. The maskant is a suitable acrylic, epoxy, or polyester resist, or the like. The layer 14 may be applied by dipping, spray coating, or electrostatic depositing, or any other coating method to produce a layer thickness of about 0.001–0.010 inch. The coated article of FIG. 2 preferably is baked at 200° F. (±10° F.) for about 15–17 minutes, or any sufficient combination of time, pressure (such as vacuum-baking) and temperature to insure the removal of water, as is customarily used in the art. Kodak Thin Film Resist® has been found to be a quite suitable maskant. To the Kodak Resist is added 2%, by weight, carbon black pigment, or other pigment described hereinbelow.

In one embodiment, the adhesion of the resist or masking agent to a metal surface of the object to be textured preferably includes of an actual chemical, ionic, or molecular bond to the metal itself. In one embodiment, the undercutting process preferably is conducted via spray impingement of the etchant, or other agitation, such as turbulence or ultrasonic cavitation, often for periods of time that are more prolonged than is generally encountered in common photofabrication. The duration of the undercutting process is dependant upon the substrate selected and the etchant system chosen. Preferably, etching lasts up to 10–15 minutes. It may exceed 20 minutes. In some embodiments of the present invention use a layer 14 of common photopolymerized polyester resist, requires cleaning and abrading of the datum surface prior to application of layer 14. As is common good practice in the metal finishing field, in some embodiments, pre-etching and pre-baking of the metal surface is sometimes required to insure the integrity of the maskant-metal bond. In one embodiment, it is desirable to remove a minute amount of surface material (preferably 0.001 inches to 0.005 inches) to insure a chemically clean and pristine metal surface. Additional embodiments include the use of a layer 14 of epoxy dip coatings, electrostatic coatings, electrophoresis coatings or other electro-deposited coatings, and spray coatings of resist or masking agents.

Dispersing an appropriate pigment or dye into a maskant layer can render the maskant laser receptive. The maskant is selected based on the wavelength of the laser, or any projected light source, to be used to produce the desired pattern of maskant 14 on surface 12. In one embodiment, in the case of an infrared laser, the resulting local heating from the absorption of laser energy selectively removes tiny areas of the resist or maskant layer 14, thereby exposing the underlying metal surface 12 of the article to the action of an etchant. Ordinary conventional photographic image and development techniques may be used with these photosensitive materials and methods. They are less suitable, however, for contoured parts, as artwork negatives cannot easily be laid upon them for exposure.

As noted above, a preferred maskant is Kodak Resist, to which is added about 2% carbon black pigment, or other pigment more particularly suited to the laser wavelength to be employed. The pigment is dispersed into the maskant in a high shear mixer until fully dispersed, or until a temperature rise of 15–20° C. is reached. The resulting maskant is applied by dipping or by spraying, spinning, brushing or electrostatically depositing onto the surface to be treated.

Selected areas 16 of the layer 14 are then removed to expose portions 18 of the datum surface 12. In one embodiment, the use of computer-directed direct laser ablation to generate programmed patterns in the maskant layer allows the application of such patterns to irregularly shaped finished goods, parts, or items which have surfaces of compound curves or radii. Such shapes are routinely encountered in implantable medical devices, such as dental post implants, hip joint assemblies, and maxillofacial prosthetics.

To generate a selected image, or array of recesses, or a fractal pattern, in a laser receptive maskant, the use of a computer-directed laser to directly ablate the maskant or etch resist layer in selected loci is preferred.

Figure 40:
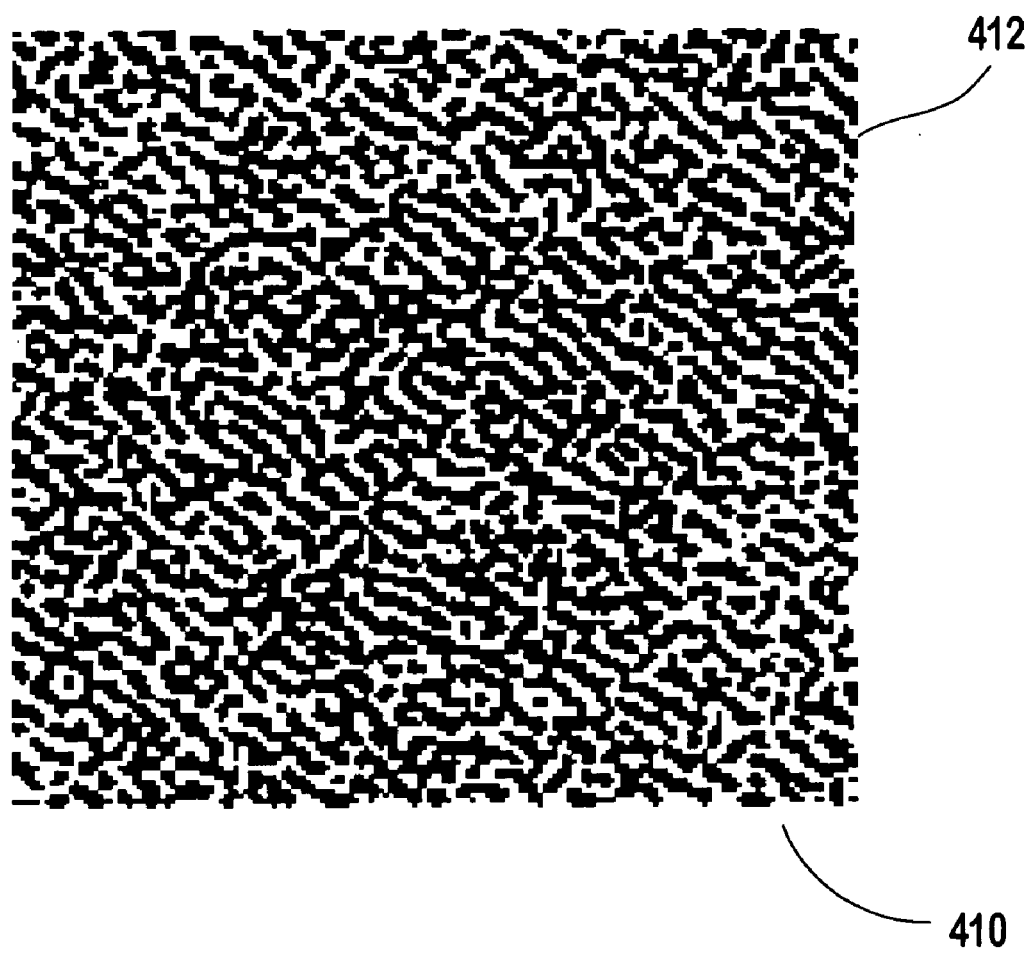
FIG. 40 illustrates a two dimensional pattern of the present invention.

FIG. 40 illustrates a preferred two-dimensional pattern 410. In one embodiment, the pattern is transferred to the surface maskant by laser ablating black regions 412. The black regions 412 are then etched with undercutting until the etched regions reach the desired complex 3-dimensional arrays of cavities. In one embodiment, the resulting patterns does not superficially resemble the starting pattern, though the resulting pattern is a derivative of the starting pattern, and/or the starting patterns basic fractal elements.

In a preferred embodiment of the method, ablations are made by direct writing with a neodymium-doped YAG laser with a wavelength of 1.06 microns, to which carbon black is receptive. A pattern is selected which optimizes the effects of undercutting. The pattern chosen is saved in Tagged Image File Format (TIFF) or as a plot (PLT) graphics file, and used to direct a laser marker.

In one embodiment, an Electrox, Scriba Nd:YAG laser marker may be used, with patterns stored in digital file format. Upon laser exposure, the underlying surface portions 18 are exposed in those areas in which the maskant absorbs the laser beam.

The pattern produced by laser ablation is predictable and can be accurately duplicated and repeated from implant to implant. While the aforementioned YAG laser has been found effective in the present invention, so also have $CO_2$, diode pump, and green lasers. Any laser capable of ablating, or thermally vaporizing, the maskant to generate a desired pattern of exposed surface may be used in carrying out the method described herein. Other methods of removing maskant include: mechanical tools, chemical milling, photochemical etching and laser eradication.

The pattern can be generated on a Computer Aided Design (CAD) system using any compatible file type, or generated as a phototool for imaging. The pattern can be scanned from a drawing, print, photograph, or the like, and converted into any file type compatible with the laser system employed.

An alternative method of manufacture is to use a photo sensitive maskant, which is applied to the device as stated above, or applied as a dry film which is laminated to the surface. The maskant is then exposed, using a light source of an appropriate wavelength (typically 280–550 nanometers). Portions of the maskant are cross-linked and/or bonded to the surface during the exposing process (in the case of negative working resist). The other areas of the maskant are dissolved or washed away in a developing process that utilizes a compatible developer solution, such as sodium or potassium carbonate, or stoddard solvents, thereby exposing the underlying material.

The exposed portions 18 of the surface 12 are etched, preferably using a spray etcher at 100° F. spray temperature and 10 lbs/in$^2$ spray pressure, in a Nitric and Hydrofluoric Acid solution for about 20 minutes. Sufficient "fresh" etchant is continuously impinged upon the etch surfaces 18 to encourage lateral, as well as vertical etching. It will be understood that alternative etching processes, such as immersing ultrasonics and electrolytic etching, can produce similar results.

In one embodiment of the present invention, the methods of replenishing the etchant at the surface being textured is required to successful practice of the invention. At the etchant/metal interface a depletion condition exists as some of the active species in the etchant are consumed by the etching action and the formation of metal salts. Because aggressive and uniform etching action is preferable to ensure development of the desired elliptical geometry of the etched cavity, a spray impingement method is frequently used. In one embodiment, such a spray method allows an off-axis or directional control to achieve the resulting textured surface and causes the undercutting to be in one or more desired directions or axes of the part (e.g., device 10) rather than another.

In a preferred embodiment, the spray etching system can be arranged so as not to impinge from all angles, or not to rotate with respect to the workpiece. For example, if a spray nozzle is affixed so as to impinge the work at a constant oblique angle to the piece being etched, then surface flow effects will control the etching process in the microscopic regions of the ablated maskant in such a way that "tilting" of the etched cavities (described in more detail below) is a consequence of the process.

Figure 4:
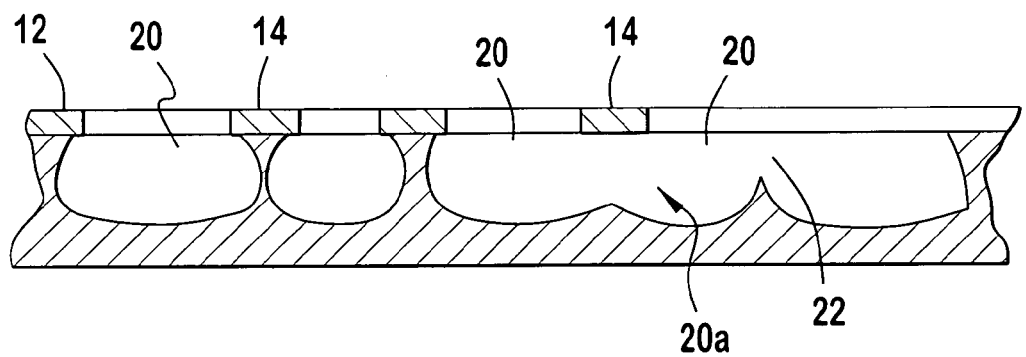
FIG. 4 is similar to FIG. 3 and showing portions of the article not covered by maskant etched away to provide undercut and interconnected recesses.
Figure 5:
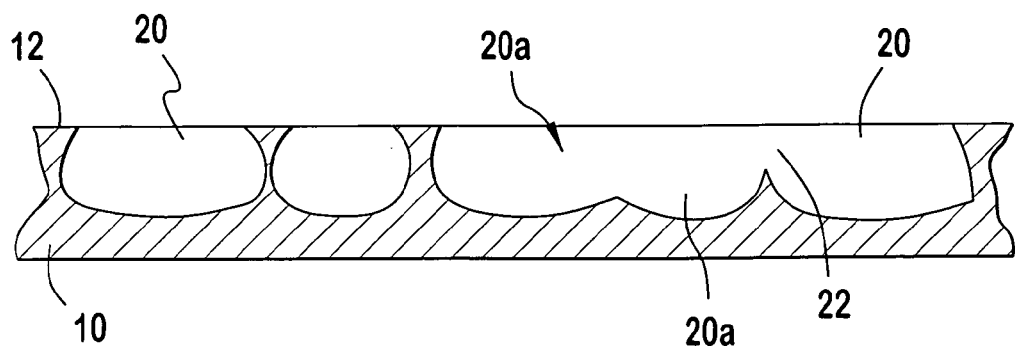
FIG. 5 is similar to FIG. 4, but showing the remaining maskant layer stripped away.
Figure 9:
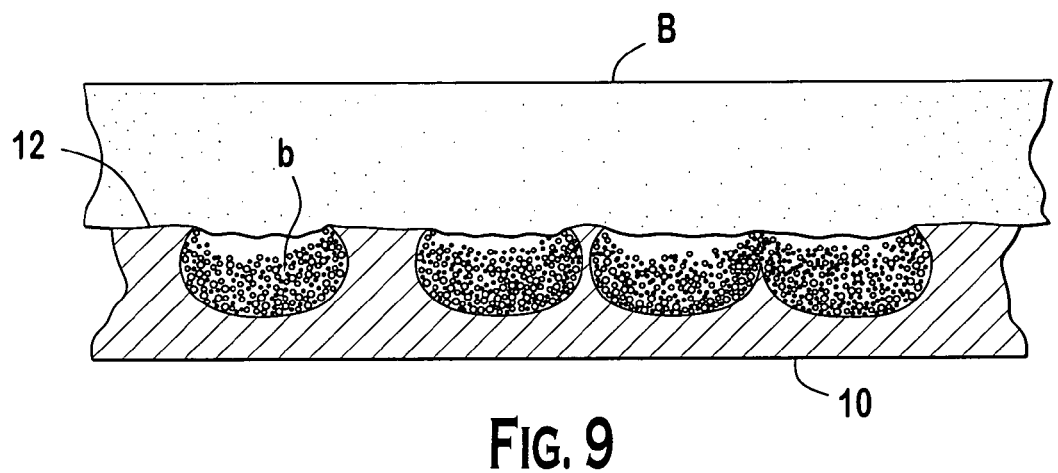
Figure 10:
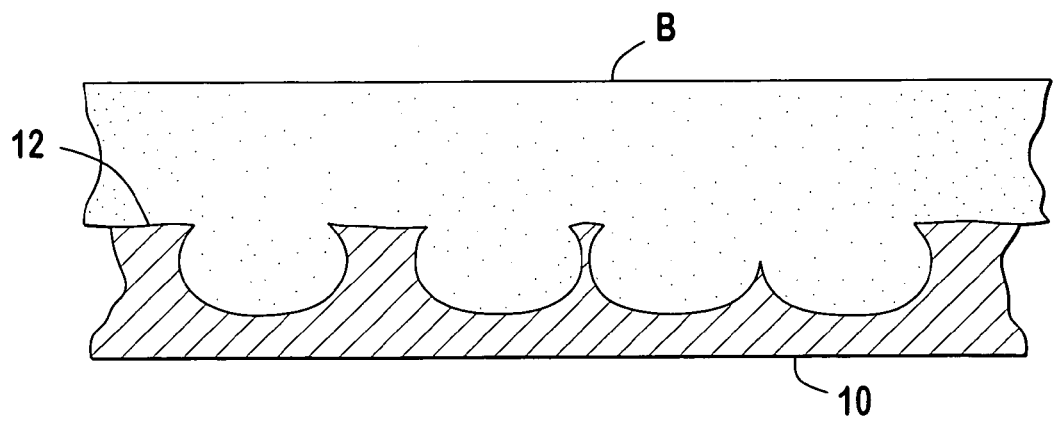

The etching produces recesses 20 which are undercut, as shown in FIG. 4, and which are, in part, interconnected, as at 22. In the preferred embodiment, the metal is etched in such a manner as to deliberately cause undercutting of the pattern, and to permit connection, joining, or "breakthrough" of some of the recesses so as to produce a sharply defined complex network structure, including an interconnecting pattern in which the size of most of the recesses is smaller at the surface 12 than at a plane some distance below the surface 12 of the article 10. The recesses 20 may, in at least some instances, interconnect at and near the surface 12, as at 22 in FIG. 4, to provide enlarged surface recesses 20a (FIG. 5).

The etching of the metal surface 12 is thus carried out in one step, as opposed to repetitive etching suggested in some of the prior art references cited hereinabove. In the preferred one-step etching process, non-spherical ovoid shaped recesses are created featuring desired sizes and depths which are repeatable from implant to implant.

The remaining resist may be removed by immersing the body surface in a NJ/Phase 23 Stripper bath at about 180° F. for about 10 minutes. Alternatively, the maskant layer may be removed (FIG. 5) by solvation or emulsification. If desired, the article 10 may be lightly post-etched.

In one embodiment, in a titanium hip joint, for example, the metal was first washed with an alkaline degreasing detergent (e.g., an Oaktite® solution), water-rinsed in deionized water and briefly pre-etched in a hydrofluoric/nitric acid etchant solution, so as to produce a chemically clean, freshly-exposed metal surface suited to maskant adhesion, water-rinsed again thoroughly, and oven dried at 110° C. prior to coating with the selected resist agent (e.g., Kodak KPFR, or any other resist, including other polymer classes, such as reactive epoxy or urethan systems, or lacquers and varnishes). A polyester resist coating was then applied by dipping, air-drying for 15 minutes, and baking at 100° C. for 20 minutes. Alternatively, an epoxy e-coating (e.g., PPG Powercron® CF-665) can be successfully used. A desired pattern may then be laser-imaged onto the surface with a 90 watt neodymium-doped YAG laser at 85% power, and at a machine setting of 3 frequency units to achieve a shallow penetration to and below the surface of the base metal. The typical depth of penetration is 10 microns. This assures the cleaning of the metal base layer to remove maskant ablation residues from the regions to be etched. The hip joint was then again baked at 100° C. prior to etching to insure full cross-linking of the polymer, and to remove low-molecular-weight pyrolysis products from the maskant polymer.

The surface of the hip joint was then etched to the desired depth. The broadest depth range is 0.1 mm to 2 mm, with a preferred depth range of 0.4 to 0.6 mm. Certain patterns may, in extreme situations on some metals require shallower or deeper etching than the preferred range, in order to develop a desired three-dimensional pattern. For example, more delicate pattern designs, may require very light etching in order to preserve the original pattern details. However, nearly all the patterns used to date have been well-formed by etch depths of 0.4 to 0.6 mm.

The depth range preferably depends on pattern coarseness. In one embodiment, coarser patterns have wider land areas (discussed below), and therefore can tolerate deeper etch depths before they are cut off by undercutting in a vertical spray etcher at 20 to 30 minutes (depending on desired depth and pattern coarseness) at 100° F.

After etching to the desired depth the article is rinsed well in running water and air dried. The article is then inspected for proper etching, sufficient undercutting, and general quality. The resist or maskant was then stripped from the hip joint using a nuphase stripper solution such as a concentrated caustic stripping solution (e.g., Oakite® Eurostrip® 704 manufactured by PC&E), at a temperature of 160° F., for 15 minutes. After stripping, the article was rinsed in deionized water and oven dried at 220° F.

In one embodiment, there is thus provided a method for producing a complex, at least in part interconnecting pattern, or similar 3-dimensional surface treatment, to enhance the attachment of biological matter to a surface of an implantable device, or the interconnection of other bodies to be bonded, made by selective etching and undercutting of a surface so as to form a network of at least in part interconnected recesses. The pattern is formed by the direct laser ablation of an etch resist or maskant layer, allowing the textured surface to be applied to items with complex or curved surface geometries. The pattern is stored in a CAD or other computer-based system which controls the maskant ablations and is predictable and subject to repetitive duplication. The article is chemically etched to form the complex pattern. The metallurgical properties of the material of the article are not altered by heat, but remain substantially consistent during the process. Soft tissue or bone may in-grow the surface so produced, resulting in an interpenetrating network that offers superior mechanical adhesion and resistance to degradation. Further, the sharp edges at the intersections of the undercut recesses and the original datum surface facilitate an initial "scratch-fit" between the implant surface and a bone.

In operation, to produce a textured surface on a surgical implant, a selected pattern of undercut and at least in part interconnected recesses is effected in a surface of the surgical implant (FIG. 5). In implantation, the implant surface 12 is pressed against the bone B, (FIG. 6) such that sharp edges 24 of the recesses effect the "scratch fit" with the bone B, which involves shaving off, or milling, particulate segments b of the bone B, which segments b enter the ovoid recesses 20 wherein, in due course, the bone segments b stimulate in-growth of the bone B (FIG. 7) to securely lock the implant to the bone B (FIG. 8).

Thus, the scratch-fit securely adjoins the implant article 10 to the bone B, to prevent or minimize micro motion between the body 10 and bone B. The presence of such motion would discourage the ingrowth of bone into the implant and thereby discourage the long-term interconnection of the implant and bone.

Further, the scratch-fit application of the implant to the bone harvests bone particulate matter which falls into the surface recesses and is retained by the recesses to encourage and stimulate ingrowth of the bone into the recesses. Inasmuch as the recesses are of an ovoid configuration, they provide a greater sub-surface fractal area than spherically shaped recesses, and thereby a greater area for engagement of the bone material and the implant.

Figure 11:
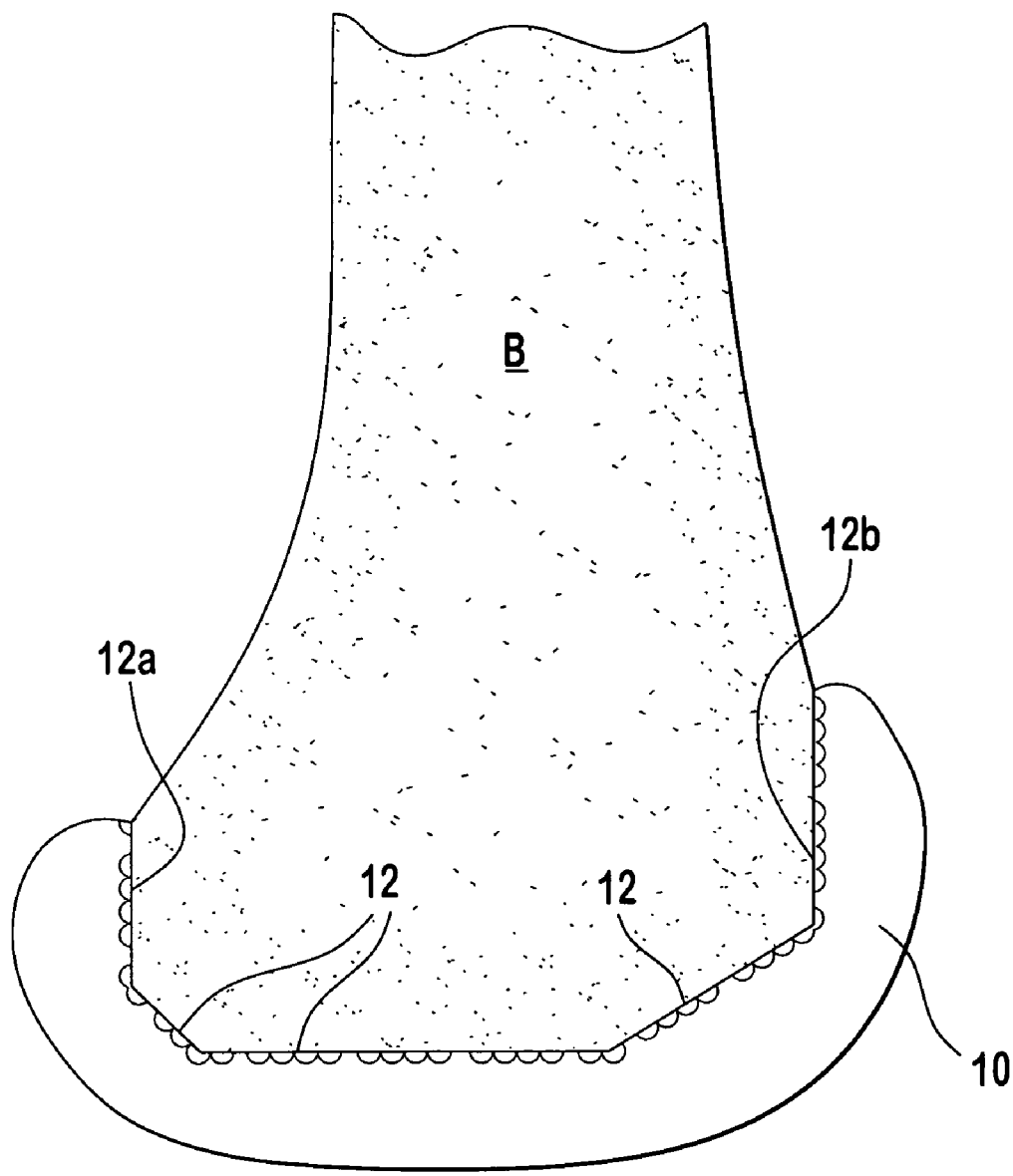
FIG. 11 is a diagrammatic sectional view of a surgical implant having a plurality of surfaces treated as illustrated in FIGS. 2–10.

Referring to FIG. 11, it will be seen that for bones B accepting an implant 10 having a plurality of datum surfaces 12, including opposed surfaces 12a and 12b, the accurate location of the datum surfaces is most critical, inasmuch as any build-up of implant material above the datum surfaces causes the implant not to be accepted by the bone B. Texturing the surfaces 12 below the surfaces 12 does not add material to surfaces 12. Whereas, texturing the surfaces 12, by adding texture above the surfaces increases the space required between the opposed bone surfaces to accept the implant and leads to rejection of the implant. Known methods of texturing by adding to a surface lack the required precise control to determine the deviation of the peaks of the added material. The method presented herein facilitates accurate and precise location of datum surfaces of surgical implants.

The milling of the host bone B may further serve to ream the bone B to the precise size and configuration of the article 10, insuring the best possible fit. Accordingly, appropriately shaped and sized burrs of the texture on article 10 are preferably furnished to pre-form a receptacle in the bone to properly receive the article 10. The scratch-fit securely adjoins the implant article 10 to the bone B, to prevent or minimize micro motion between the implant 10 and bone B. The presence of such motion would discourage the ingrowth of bone into the implant and thereby discourage the long-term interconnection of the implant 10 and bone B.

In some embodiments, a device with a textured surface according to the present invention, can affect a self-fitting function. For example, it will be appreciated that where a textured surface, according to the present invention, is applied to an acetabular cup, the cup itself can be used as a reaming tool, effecting a perfect fit to the host bone and shortening healing time. Further, in the process of self-fitting, there is milled, or harvested, fine bone particulates, or pulp, from the patients' own body, for example, as shown in FIGS. 6–10. The resulting material is forced into the recesses to serve as a nucleation host for a spontaneous homograft completed by the attraction and growth of the patient's osteoblasts, providing a strong bond and longer installed lifetime.

Figure 12:
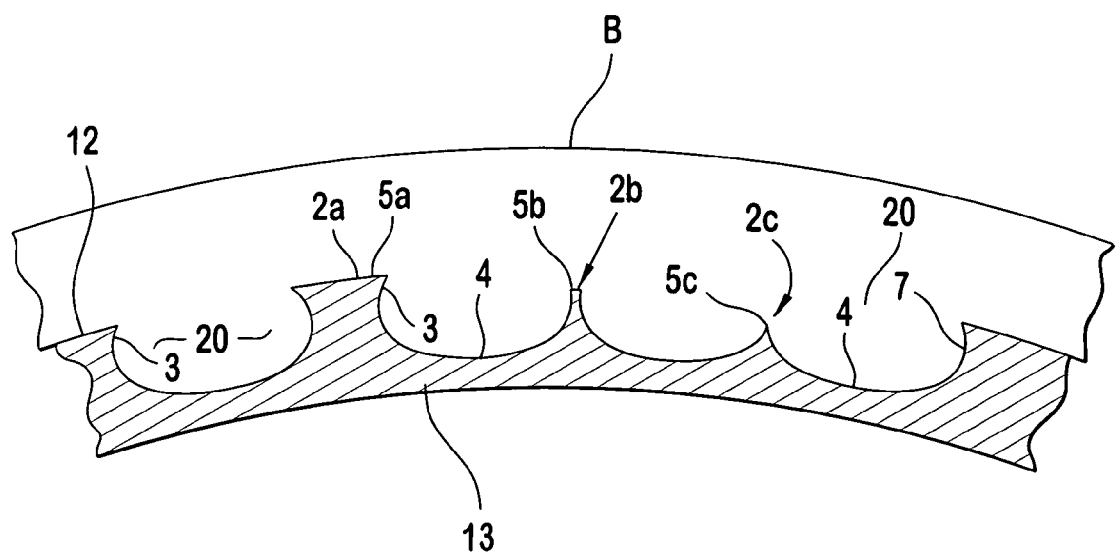
FIG. 12 is a diagrammatic sectional view of structural features of the a surface texture.

Some embodiments of the present invention may incorporate sharp-edged geometry such as at undercut 3 (See FIG. 12). It may be desirable for the sharp-edged undercut geometry to be later modified by a subsequent dulling process so as to causes sharp edges to be rounded. For example, abrasive blasting, glass bead blasting, or a subsequent acid etch all may be used to slightly dull or "break" the original sharp edges, if desired. Such a subsequent dulling process may include, for example, etching, polishing (e.g., electropolishing), abrasive reduction, buffing, and honing. Through this process, at least some of the walls 7 (shown on FIG. 14 and described in more detail below) may become perpendicular to the surface of the article, or may actually diverge outward from each other as they approach the surface of the texture pattern. In some embodiments, post-processing (e.g., cleaning or polishing) defeats the benefits of the textured surface. Still, some practitioners may incorporate a post-processing step.

Figure 14:
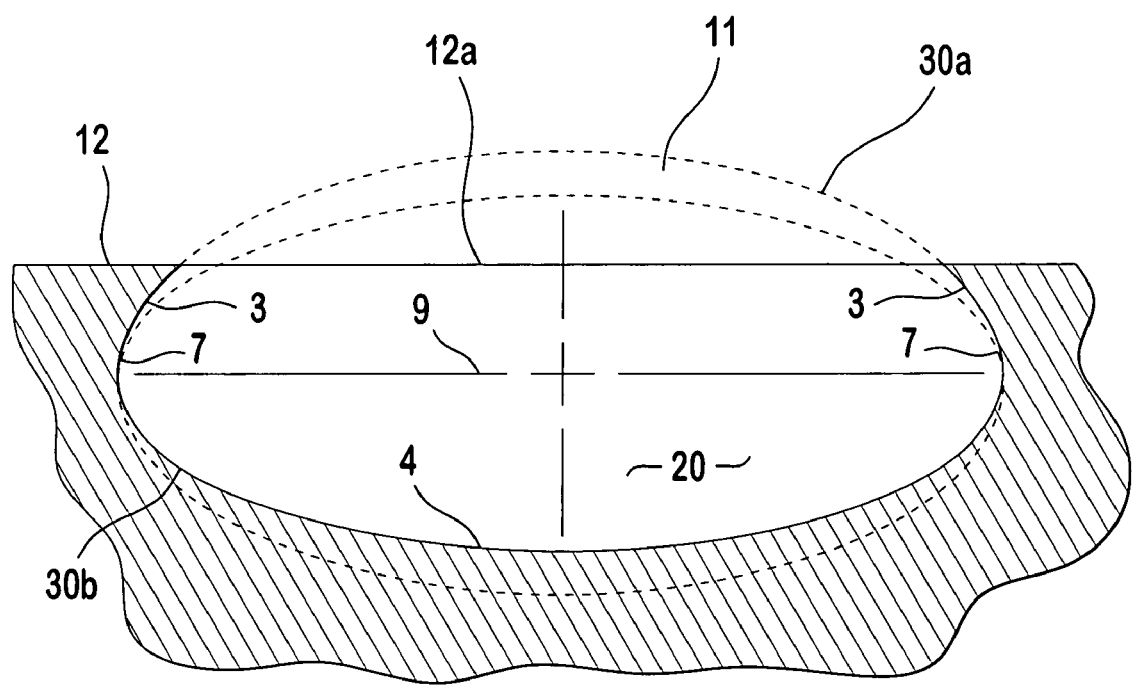
FIG. 14 is a diagrammatic sectional view of a complex ellipsoid.
Figure 15A:
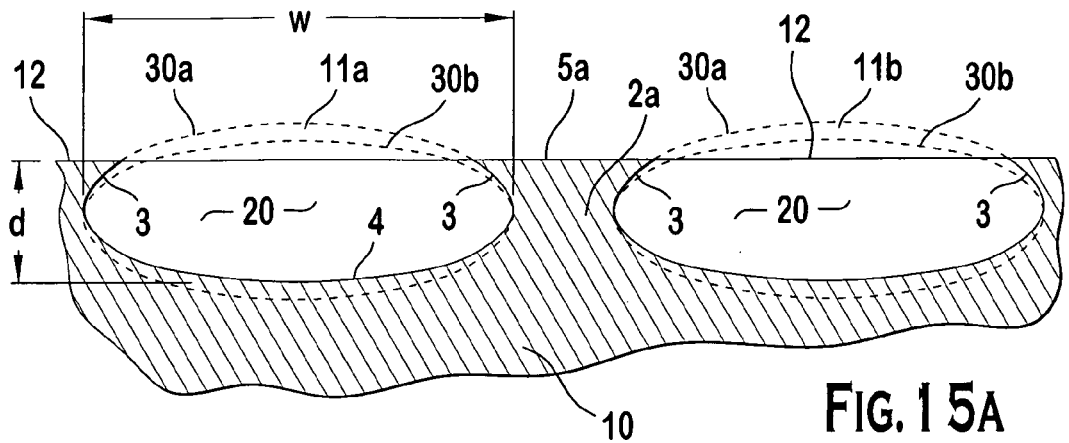
FIGS. 15a–15c illustrate diagrammatic sectional views off structural features of a textured surface.
Figure 15B:
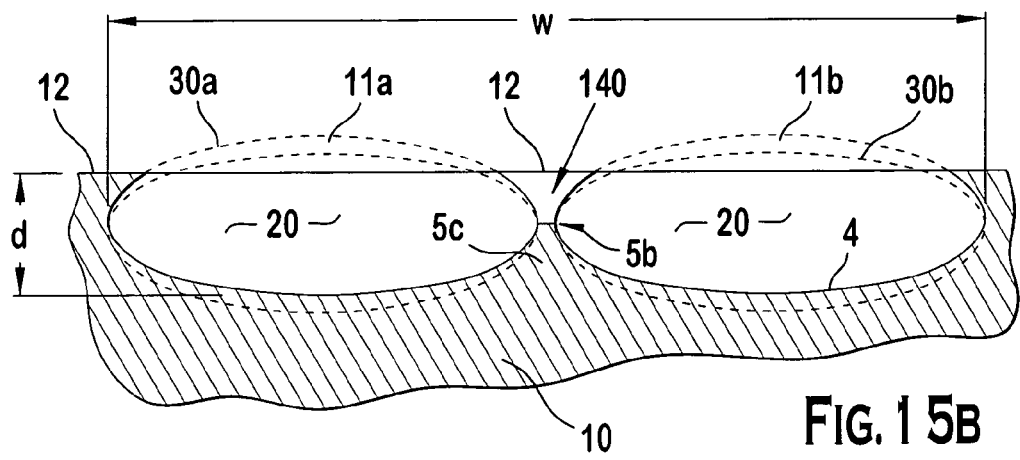
Figure 15C:
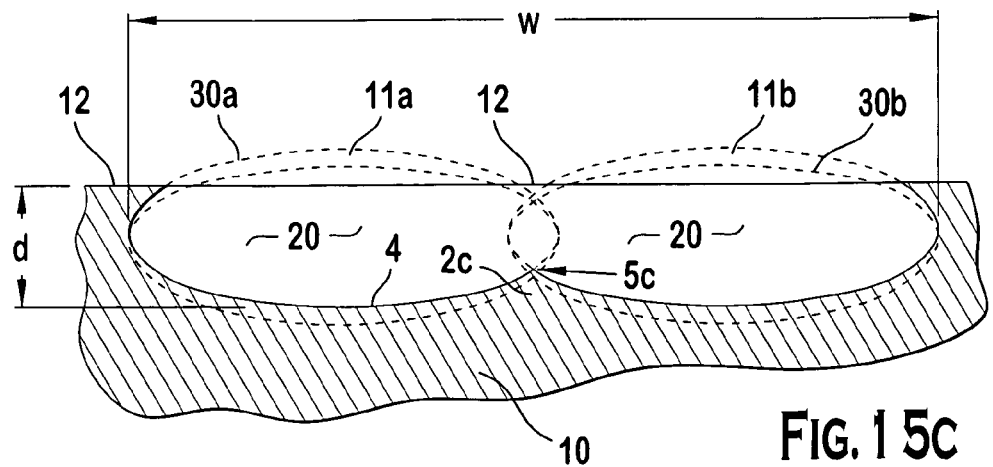

Looking in more detail at formed features according to some exemplary embodiments of the present invention, FIG. 14 illustrates a preferred geometry of a cavity 20 which has been deliberately produced with the geometry of a complex ellipsoid. A complex ellipsoid is preferably derived from two or more ellipsoids. In a preferred embodiment, the complex ellipsoid is derived from at least two non-spherical ellipsoids. Alternative embodiments may include combinations of spherical and non-spherical ellipsoids. The complex ellipsoids may be a combination of ellipsoid 30a and ellipsoid 30b. The complex ellipsoids may alternatively combine three or more ellipsoids with three or more different angular projections. More particularly, a geometric shape of the illustrated cavity 20 may be described as being defined, at least in part, by two non-spherical ellipsoids sharing a major axis 9 and having varying angular projections (e.g., an ellipse having a 40 degree protection, superimposed on an ellipse having a 50 degree projection, or any combination of ellipses from about 9 degrees to about 89 degrees so as to produce a species of the complex ellipse shape).

Ellipsoid 30b with a narrower angular projection defines a bottom 4 of cavity 20. Ellipsoid 30a with a wider angular projection defines an arched undercut 3 which is contiguous with wall 7 and bottom 4. In the preferred embodiment wall 7 and bottom 4 are concave and contiguous. Cavity 20 (FIG. 16) may be further characterized as having a ratio of cavity width, w, to cavity depth, d, that is greater than or equal to unity. The preferable width:depth ratio ranges from 1:1 to 9:1. In a preferred embodiment, the ratio is approximately 4:1.

Referring now to FIGS. 12, 14, 15a, 15b, and 15c, protrusions 2a, 2b, and 2c have differing geometries each of which is preferably defined by the relationship between at least two complex ellipsoids. Protrusions 2a, 2b, and 2c extend from bottom surface 4 of cavity 20 toward datum 12. Protrusion 2a has a peak 5a in the form of a plateau or mesa which is coincident with outer surface 12. Complex ellipsoids 11a and 11b define the lateral dimensions of protrusion 2a. Cavity 20 is also defined by complex ellipsoids 11a and 11b which intersect datum 12 to create cavity 20 in outer surface 12. The portion of outer surface 12 remaining untouched by the ellipsoids 11a, 11b defines peak 5a. An ellipsoid forming protrusion 2a preferably forms an undercut 3 at the face of the protrusion.

Protrusion 2c has a sub-peak 5c located between datum 12 and bottom 4. Sub-peak 5c is defined by the intersection point of at least two complex ellipsoids 11. In a preferred embodiment, protrusion 2c is formed from the at least two complex ellipsoids 11a, 11b, which overlap to the extent that no overhang is created in wall 7 of protrusion 2c. In some embodiments the overlapping of ellipsoids may result in an overhang on one face of the protrusion but not on another face of the same protrusions.

Protrusion 2b has an intermediate peak 5b which is also located between datum 12a and bottom 4. Intermediate-peak 5b is preferably defined by two or more complex ellipsoids 11a and 11b that do not overlap. The complex ellipsoids 11a, 11b that at least partially define intermediate-peak 5c, however, are in close enough proximity to each other that the portion 140 of article 10 that previously existed between intermediate-peak 5c and datum 12a can be predicted to break-off during manufacture such as, for example, during polishing of the etched product, leaving an intermediate peak 5c. In one embodiment, the surface is "softened" by common buffing or polishing methods (as described above). Thus, in one embodiment, the surface is modified such that the sharp edges will be removed, as well as some of the tops of the projections.

Figure 16:
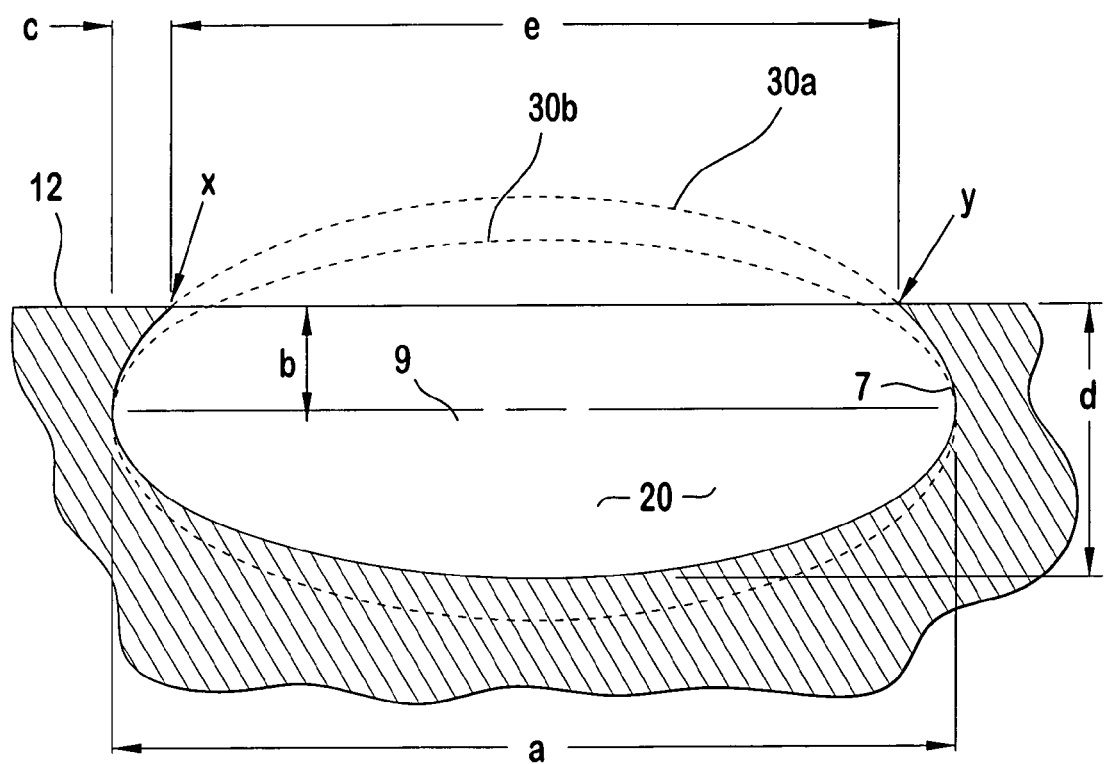
FIG. 16 is a diagrammatic sectional view of a complex ellipsoid.
Figure 16A:
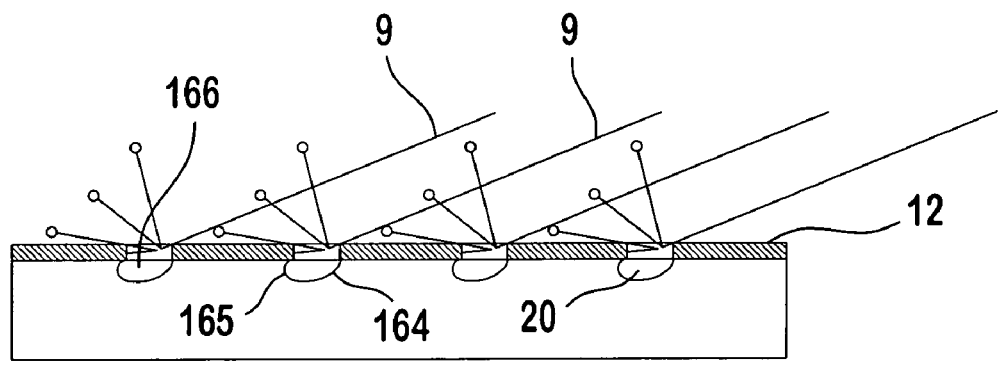
FIG. 16A is a diagrammatic sectional view showing an embodiment of complex ellipsoids with an oblique orientation.
Figure 16B:
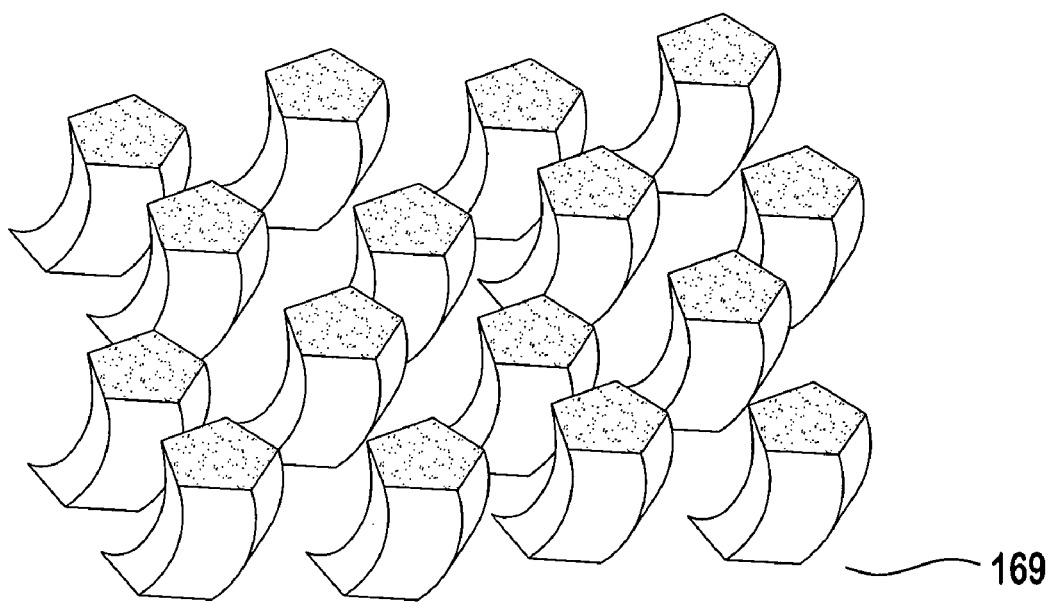
FIG. 16B illustrates an exemplary textured structure.

For clarity, FIGS. 14 and 16 shows the major axis 9 substantially parallel with datum surface 12. Orientation of the major axis may vary from perpendicular to parallel depending on the desired finished texture, the pattern of the desired texture and direction of the texture. Preferred embodiments have an orientation of axis 9 that varies between 90 degrees and 70 degrees relative to datum 12. In one embodiment, for example, axis 9 is oblique to datum surface 12 (shown in FIG. 16A). This is preferably achieved by impinging etchant at an acute angle to datum surface 12. In one embodiment there is achieved an asymmetrical undercut pattern that is characterized by an undercut face 165, of ellipsoid 166, that projects over cavity 20 a distance greater than the projection of the opposing face 164. In one embodiment, opposing face 164 does not overhang cavity 12. In one embodiment, the impingement of etchant at an angle produces a tilted saw-tooth or tiger-tooth structure 169 shown in FIG. 16B. Such structure allows relatively easy insertion into a bone channel 168 (e.g., when insertion is in a direction such that undercut 165 is not urged into bone B as in FIG. 16C), but strongly resists tensile force urging dislodgment of the implant (e.g., when removal is in a direction such that undercut 165 is urged into bone B as in FIG. 16D). In one embodiment, cavities 20 are aligned in series so that a cross-section of the textured surface has a regular pattern which may also be a repeating pattern (see, e.g., FIGS. 16C, 16D), 42A and 42B).

FIGS. 42A and 42B illustrate a comparison between the affects of directional and nondirectional impingement. FIG.

Figure 16C:
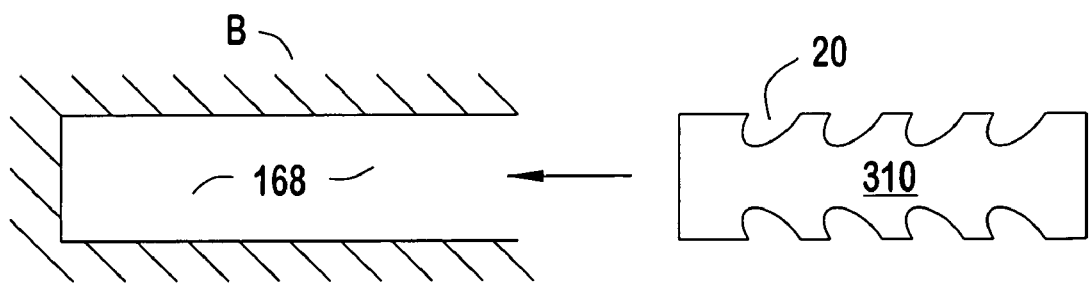
FIG. 16C-16D are diagrammatic sectional views of a textured structure being inserted into a bone channel.
Figure 16D:
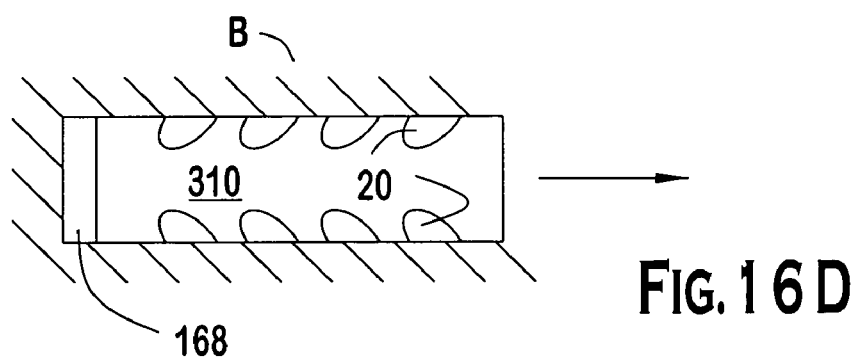

42B illustrates an embodiment of the invention where nondirectional impingement has been performed. In a preferred embodiment employing nondirectional impingement, the major axis 9 of complex ellipsoid 30 is substantially parallel with datum surface 12, and undercuts are present at the point 432 where the cross section of ellipsoid 30 intersects datum 12. In another embodiment illustrated in FIG. 42A, major axis 9 is oriented oblique to datum surface 12, there is an undercut 432 at the distal end 431 of cavity 20, and face 434 has no undercut at the proximate end 433 of cavity 20. In one embodiment, cavity 20, formed by directional etching, is defined by a concave surface 432 and a convex surface 434. Alternatively, opposing surfaces of cavity 20 may each have concave configurations (FIGS. 16C and 16D).

Figure 41:
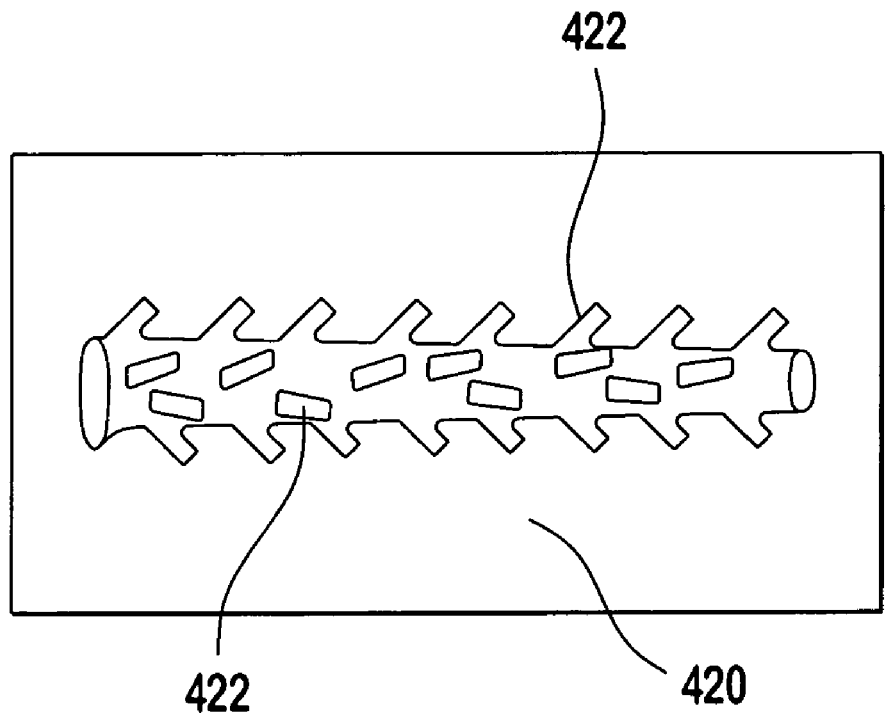
FIG. 41 is a diagrammatic illustration of a barbed implant.

In one embodiment of implant 40 (illustrated in FIG. 41), unidirectional barbs 422 are produced in the surface that can be inserted into bone or tissue. The directional orientation of barbs 422 make it difficult to withdraw from the bone or tissue. In conditions where a directional or anisotropic geometry are not desired, simpler non-directional agitation such as a turbulently-flowing etchant bath, or ultrasonic cavitation can be employed.

FIG. 16 illustrates a preferred geometric relationship between surface 12 and ellipsoids 30a and 30b. The dimensions are typical and descriptive of a commonly achieved pattern, but are not restrictive. The skilled practitioner may vary these dimensions greatly depending on the desired outcome. In the embodiment illustrated, depth d of cavity 20 as measured from the datum 12a to bottom 4 is substantially 0.0210 inches. Major diameter a of ellipsoids 30a and 30b is substantially 0.0474. The distance b from datum 12 to the major axis 9 is substantially 0.0055 inches. Distance c along the major axis 9 between the perimeter of complex ellipsoid 30a to a point x projecting from the intersection of complex ellipsoid 30a with datum 12a is substantially 0.0012 inches. It follows, that distance e along major axis 9 between projection points x and y is substantially 0.0450 inches.

Figure 13:
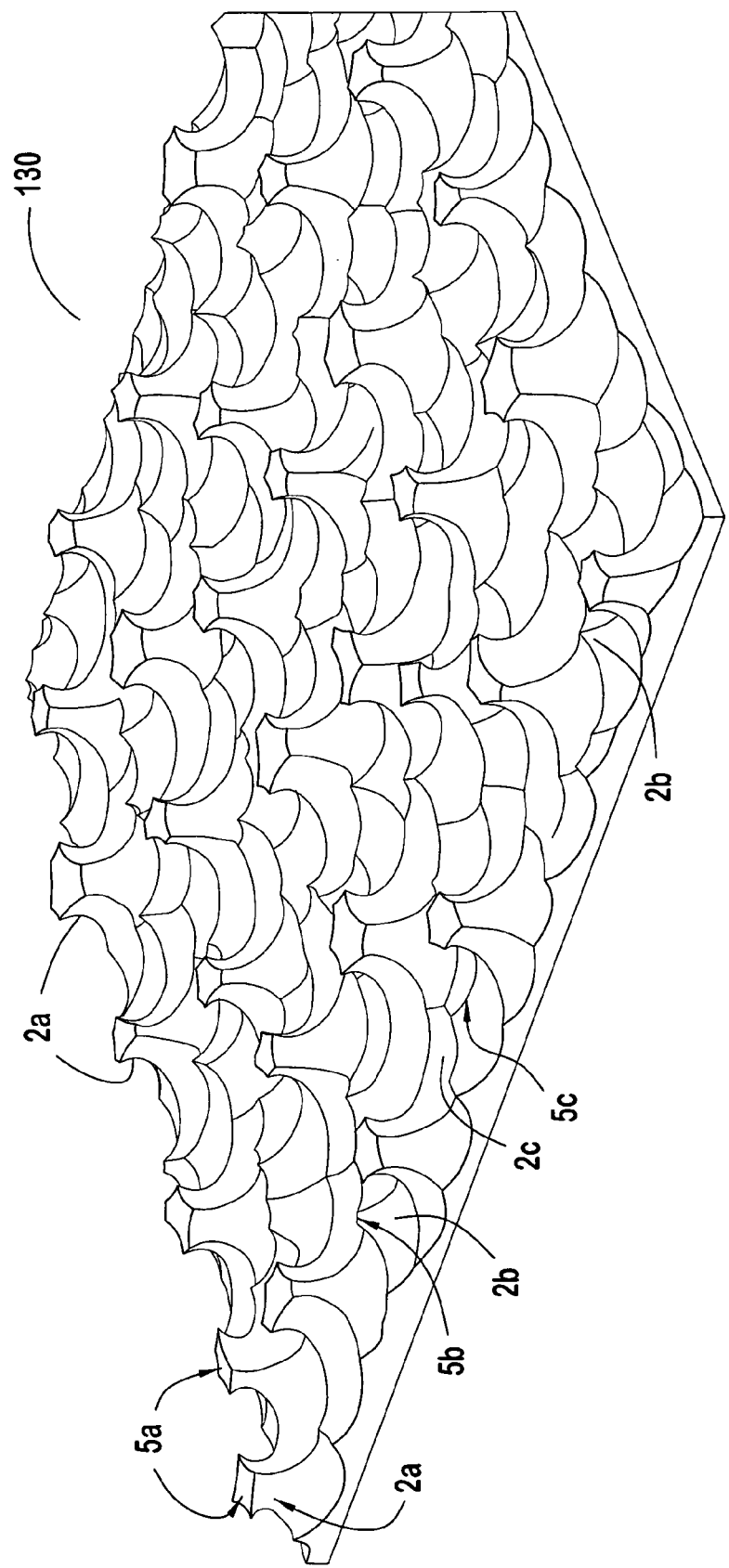
FIG. 13 is a three-dimensional illustration of a textured pattern.

Returning to FIG. 13, there is illustrated preferred three dimensional texture 130. Texture 130 is embodied in an article 10 after the etching process described above. In this embodiment, while three dimensional pattern 130 may be of an irregular pattern to the extent that the structural features of the pattern are unevenly distributed on a micro-level, this pattern is both repeatable across the device, and reproducible between devices.

The repeatable and reproducible nature of texture 130 is achievable through the employment of patterns (e.g., pattern 400 in FIG. 40) which may be seen by an observer. In one embodiment, the patterns are written into or through the maskant or etch resist layer by a laser as described herein. In another embodiment, the pattern is displayed as an image that can be seen by an observer on a computer monitor, printed output, or other such viewing device.

In one embodiment, pattern 400 may be derived from an initial pattern having a regular series of elements that include one or more regular or irregular geometric configurations such as circular dots, squares, prisms, parallelepipeds, trapezoids, triangles, hexagons, and other such geometric shapes that the practitioner deems suitable to generate the third-dimension development of the desired finished texture 130. In one embodiment, a pattern of repeated fractals or other pseudorandom network of elements are employed to generate the initial pattern. In practice when patterns are developed into three-dimensional patterns 130 by etching, they generally regularize rather than randomize. For example, an array of dots or other shapes will form boundaries as the surrounding material is removed by etching. When a connection density of portions of the etched surface peaks, sub-peaks, and intermediate peaks of approximately 58% is reached, a phenomenon known as "percolation threshold" forms, where networks of connections form.

Figure 17A:
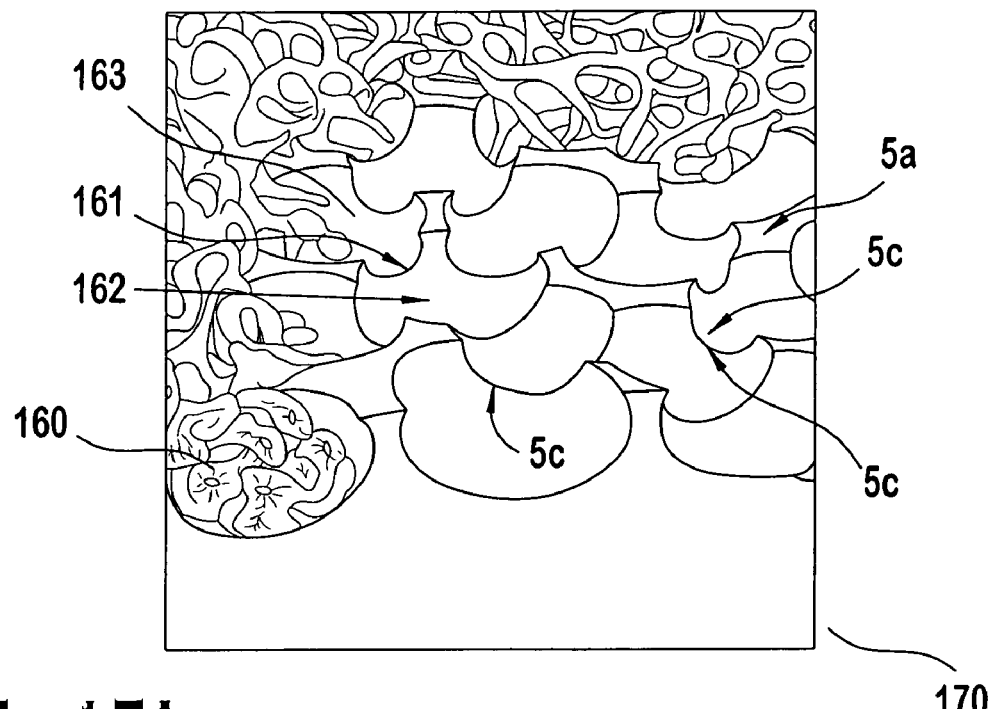
FIGS. 17A–17E are three-dimensional illustrations of exemplary textures.

FIGS. 17A, 17B, 17C, 17D, and 17E illustrate variations on the textured surface of the preferred embodiment. FIG. 17A illustrates textured surface 170 having a three-dimensional irregular pattern that is characterized by multiple intersections of complex non-spherical ellipsoids that form peaks 5a and 5c. There is illustrated sub-peak 161 which is defined by a the intersection of at least two complex ellipsoids. A first complex ellipsoid defining sub-peak 161 further defines, at least a portion of cavity 162. A second complex ellipsoid defining at least a portion of cavity 163, intersects the first complex ellipsoid to define sub-peak 161. This configuration further illustrates a resulting texture where intersecting complex ellipsoids of varying angular projections are oriented with major axes at an offset angle to one another. For example, if the initial pattern used includes elongated elements, or sets of two or more dots, a first set oriented at one angle to a grid, and a second set oriented at another angle, then the etching and undercutting process will generate a series of ovoid shapes as viewed from the top, with long axes aligned to these grid lines. For example, one set of grid lines may be at an angle of 40 degrees to the other, resulting in a lozenge-shaped array.

Also illustrated in FIG. 17A is the effect of a scratch-fit where soft tissue shavings 160 have migrated into the voids 20 and are growing to fill the voids.

Figure 17B:
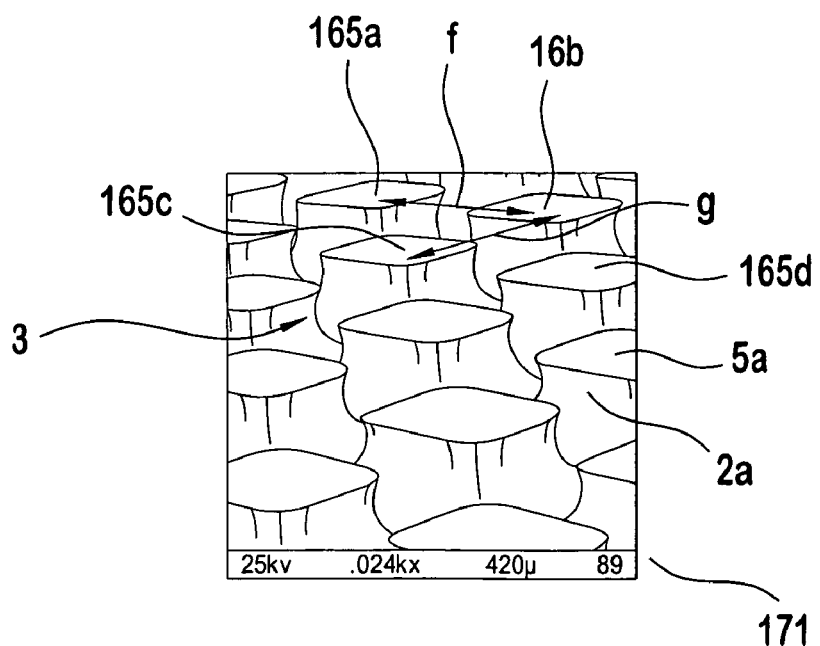

FIG. 17B illustrates textured surface 171 having a regular pattern. Each protrusion 2a in FIG. 17B has peak 5a coincident with outer surface 12 (not illustrated). There is furthermore, a geometry characterizing protrusion 2a that is defined by four (4) complex ellipsoids which have been uniformly oriented. Further characterizing this embodiment is a distance, f, between protrusions that is uniform among transverse and longitudinally adjoining protrusions. In this embodiment, distance f between protrusion 165a and 165b is substantially the same as the distance, g, between 165b and 165c. In alternative uniform embodiments, the distance between transversely adjacent protrusions may be different from the distance between longitudinally adjacent protrusions thus forming a "rectangular pattern" as opposed to a "square pattern". Any other geometrically uniform patterns are also within the scope of this invention. These include, as examples, ellipsoidal cavities substantially arranged on a hexagonal, pentagonal, triangular, or other regular geometric lattice.

Figure 17C:
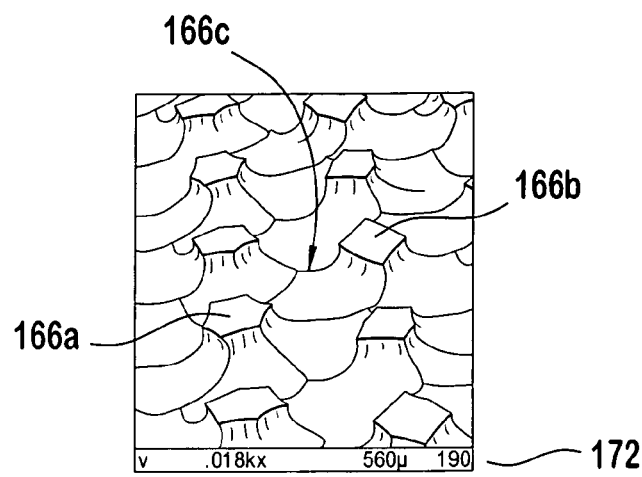

FIG. 17C illustrates a uniform repeating pattern that combines a plurality of protrusion geometries including protrusions 166a defined by five (5) complex ellipsoids; protrusions 166b defined by four complex ellipsoids; and sub-peaks 166c defined by three complex ellipsoids 166c. In this embodiment, the horizontal orientation of adjoining protrusions varies in a substantially non-random pattern.

Figure 17D:
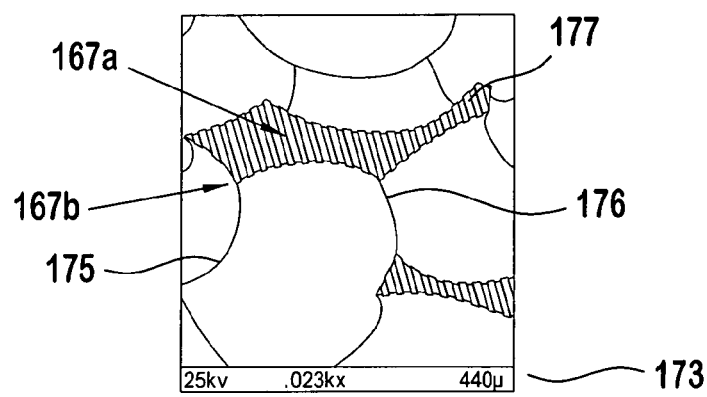

FIG. 17D illustrates protrusion 167b that is defined by a multiplicity of complex ellipsoids. Protrusion 167b has peak 167a that has been formed to project a scalloped surface 177. There is also shown intermediate peak 175 and sub-peak 176. In this embodiment, intermediate peak 175 has one face that is not undercut, or with undercut regions have been etched away in the process, and another face that is undercut.

Figure 17E:
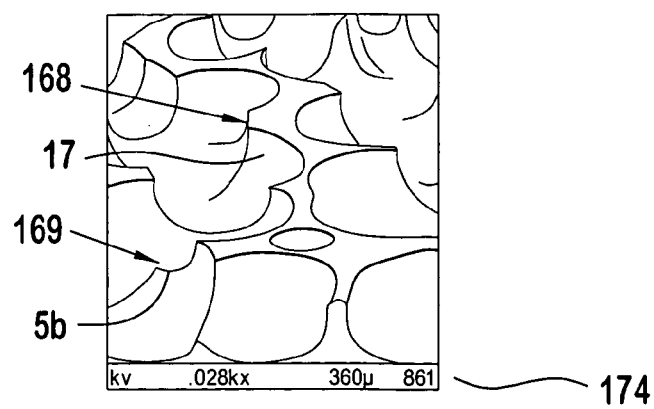

FIG. 17E illustrates protrusion 168 that has been defined by a multiplicity of complex ellipsoids. In one embodiment, protrusion 168 extends for a predetermined length of the surface. In one embodiment, the predetermined length forms a rib. The top of rib 168 is preferably coincident with the datum surface 12. In other embodiments rib 168 has a sub peak or an intermediate peak. Alternatively, rib 168 has a combination of peaks, sub-peaks, and intermediate peaks. In this embodiment, each face 17 of protrusion 168 has an undercut surface. There is also illustrated protrusion 169 which is characterized by an intermediate peak 5b that was formed when the base material above the peak was broken-off, or where a top section became isolated or cut away by the interception of undercut regions.

While some textured surface applications benefit from an undercut textured embodiments, the methods of the present invention can be used to create engineered articles. For example, certain embodiments are suited for creating an implant article having a mesh-and plate-surface (described below). In other embodiments, undercut textured surfaces are combined with mesh-and-plate surfaces.

Figure 18:
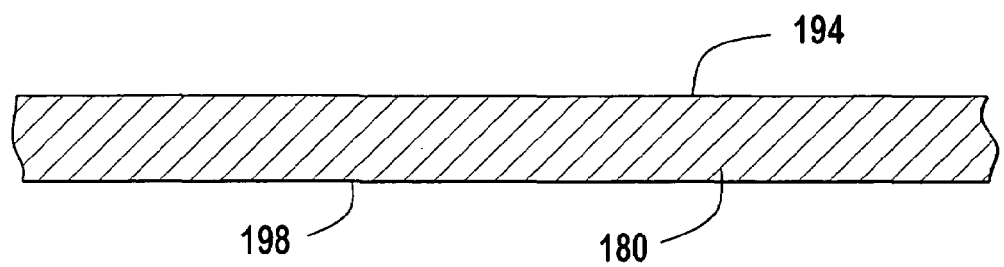
FIGS. 18–27 are diagrammatic cross-sectional views of successive stages in the making of a mesh-and-plate implant in accordance with an embodiment of the invention.
Figure 19:
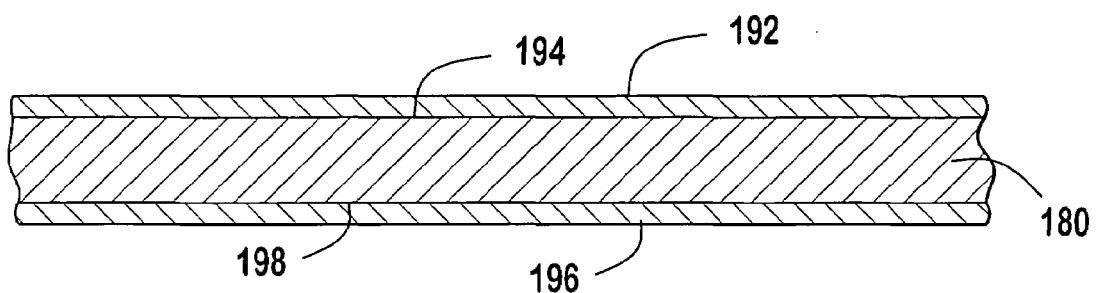

To make a mesh-and-plate surgical implant, there is provided a thin sheet 180 (FIG. 18) of tissue and bone compatible metal, such as titanium. A maskant layer 192 (FIG. 19) is applied to a first face 194 of the sheet 180 and a maskant layer 196 is applied to a second face 198 of the sheet 180. The maskant layers 192, 196 cover substantially the entirety of the first and second faces 194, 198, respectively. The maskant layers 192, 196 are resistant to chemical attack. It has been found that a photo-chemical resist, such as duPont Riston®, or Kodak Thin Film Resist®, serve as appropriate materials for the maskant layers 192, 196.

Figure 20:
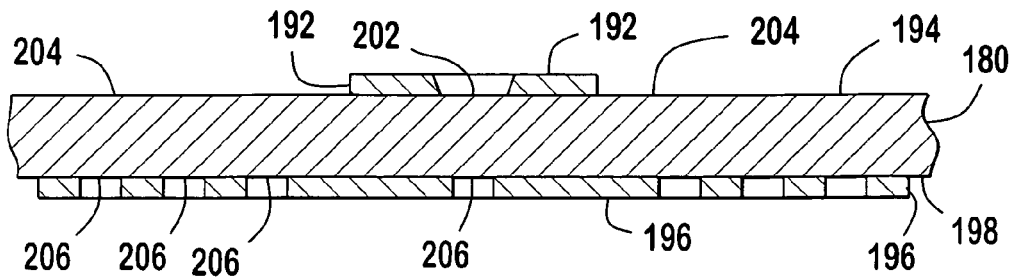

The maskant layers 192, 196 are then in part ablated from selected portions of the metal faces 194, 198 (FIG. 20), as by mechanical tools, chemical milling, photo-chemical etching, or by laser eradication, to expose portions 202, 204, 206 of the respective metal faces 194, 198 in desired patterns, ready for etching.

Figure 21:
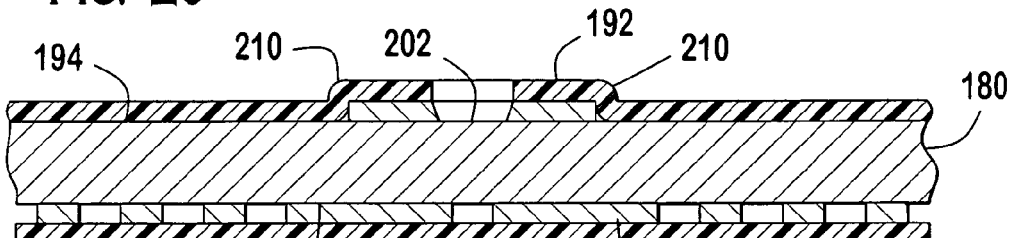

Referring to FIG. 21, it will be seen that the exposed portions 204 of the first face 194 and the maskant layer 192 on the first face 194 are covered with a protective tape 210, leaving exposed only the region 202 where a central through-hole is desired for acceptance of a mounting screw (not shown). Similarly, the exposed portions 206 of the second face 198 and the maskant layer 196 on the second face 198 are covered with a protective tape 212. The tapes 210, 212 may be 3M Brand Type #1280 Platers Tape.

The through-hole region 202 is then subjected to etching, for example, as by spray or immersion, using an acid bath of a mixture of nitric and hydrofluoride acid. It is preferred, during the etching process, to periodically remove sheet 180 from the etching process and rinse, dry and bake the sheet to maintain the integrity of the maskant and allow for in-process inspections.

Figure 22:
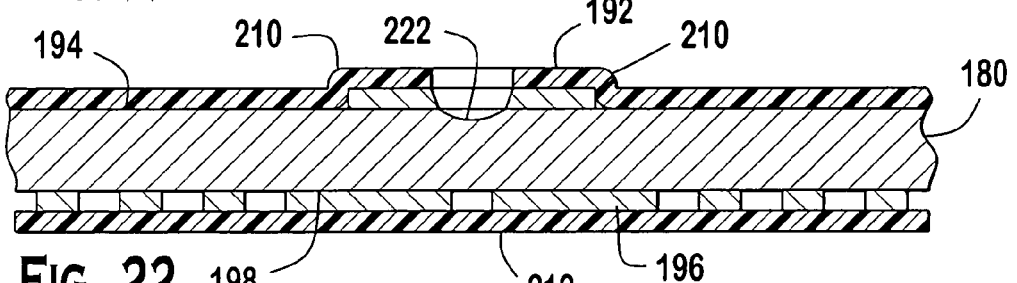
Figure 23:
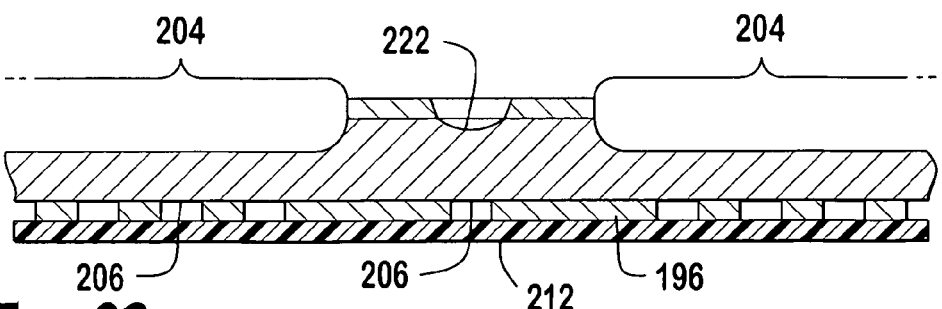
Figure 24:
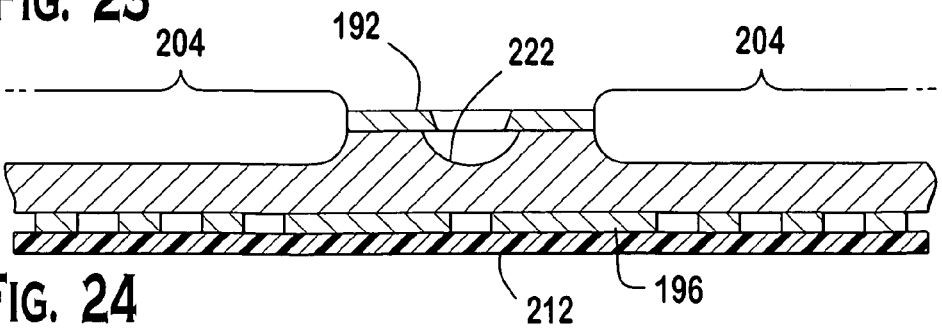
Figure 25:
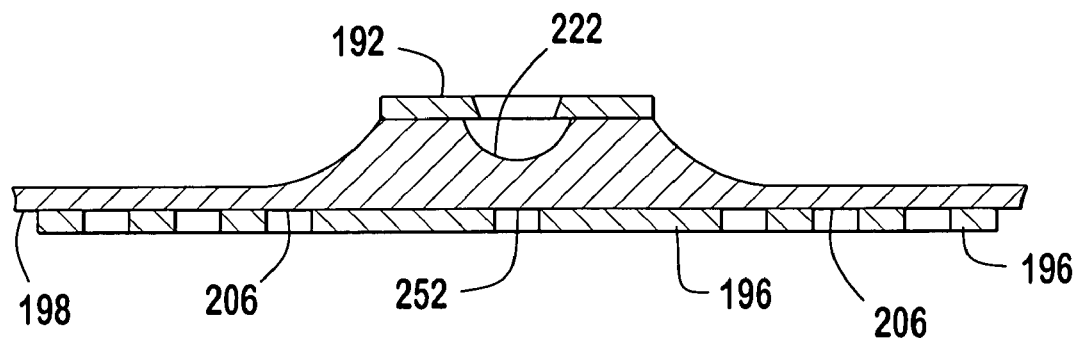

When the etchant reaching the exposed surface 202 has created a shallow crater 222 (FIG. 22), the protective tape 210 is removed (FIG. 23) and the etching of the crater 222 is resumed, and etching of the exposed portions 204, constituting the mesh portion of the implant, is undertaken. As etching proceeds, the exposed metal regions 222 and 204 are progressively removed by the etchant (FIG. 24). The etching continues until the removal of metal from the first face 194 and crater 222 has reached the predetermined extent desired (FIG. 25).

The second tape 212 is then removed, exposing the maskant layer 196 and exposed portions 206 on the second face 198, including an area 252 opposite the crater 222.

Figure 26:
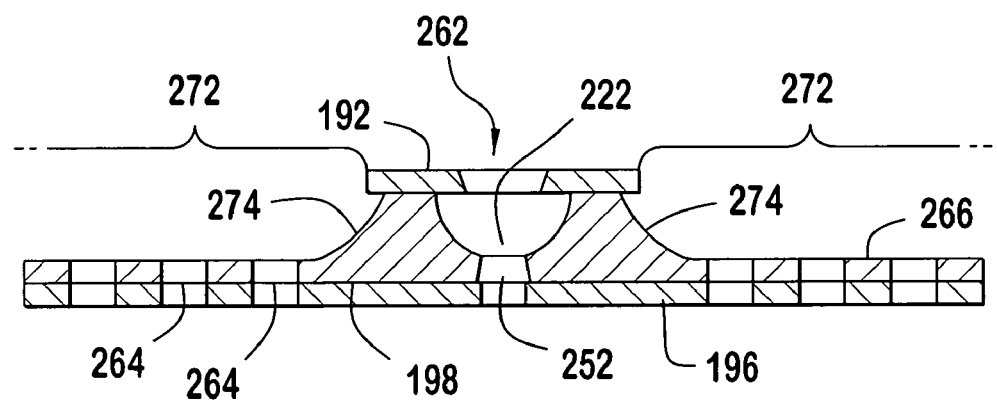

Etching of the through-hole area 252 in the sheet face 198 breaks through to the crater 222 to effect a counter-sunk through-hole 262 (FIG. 26) and second face openings 264 in communication with the newly etched first face 266.

Figure 27:
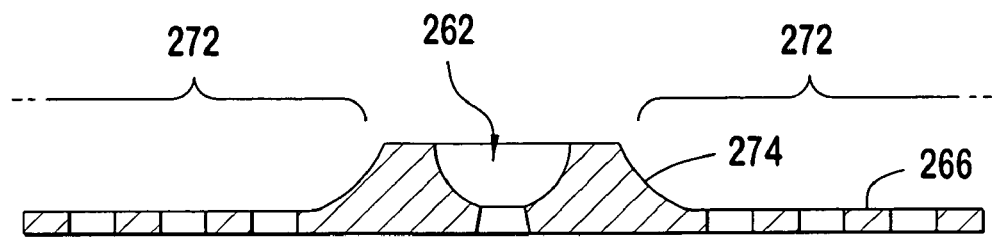

The first and second maskant layers 192, 196 are then removed (FIG. 27), leaving an implant device having the mesh portion 272, a plate portion 274, and at least one through-hole 262 for receiving a mounting screw.

Figure 28:
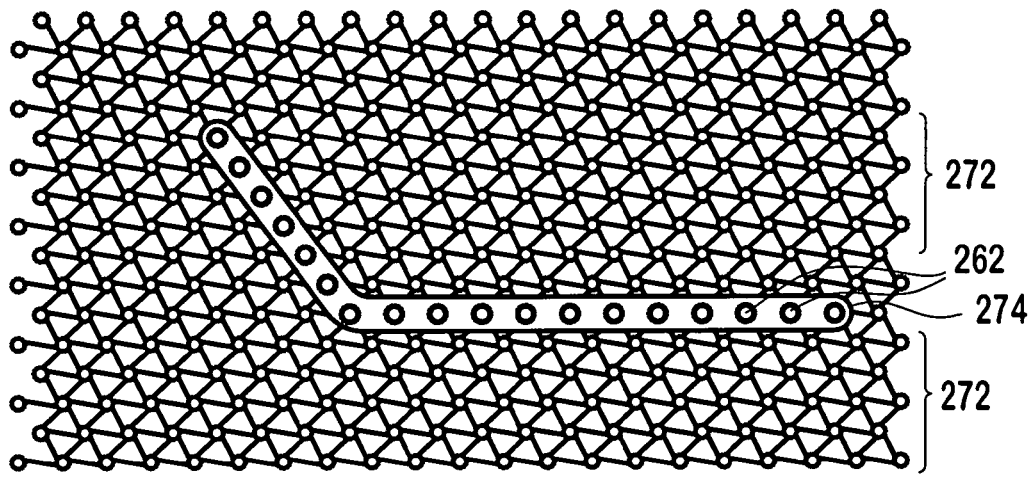
FIG. 28 is a top plan view of a mesh-and-plate implant made in accordance with the method illustrated in FIGS. 18–27.
Figure 29:
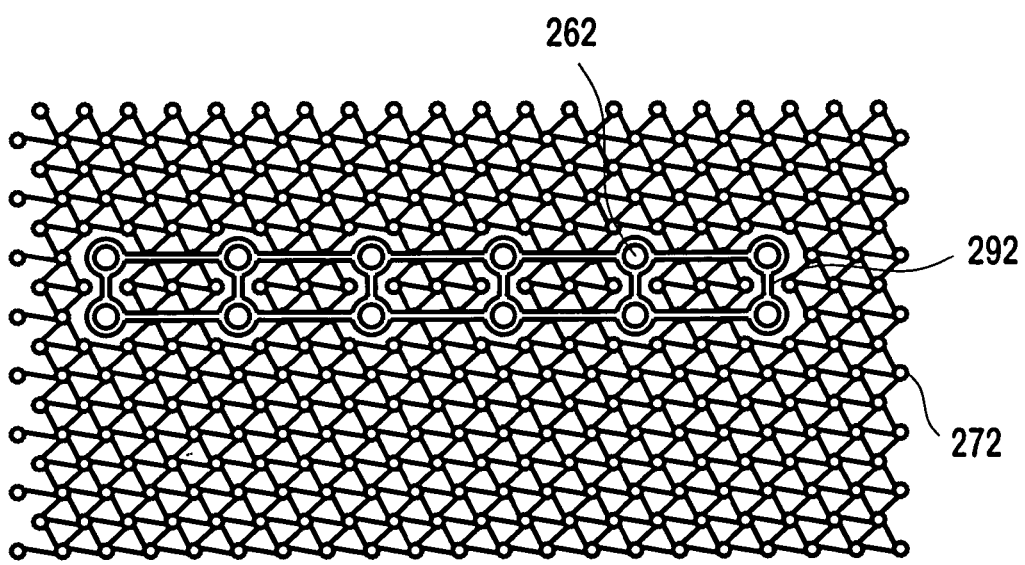
FIG. 29 is similar to FIG. 28, but illustrative of an alternative implant.

In FIG. 28 there is shown, for illustrative purposes, a dog-leg plate portion 274 having one or more through-holes 272 therein, the plate portion 274 being bounded by the mesh portion 272. In FIG. 29 there is shown a divided plate 292 having through-holes 262 therein, and bounded by the mesh portion 272.

Figure 30:
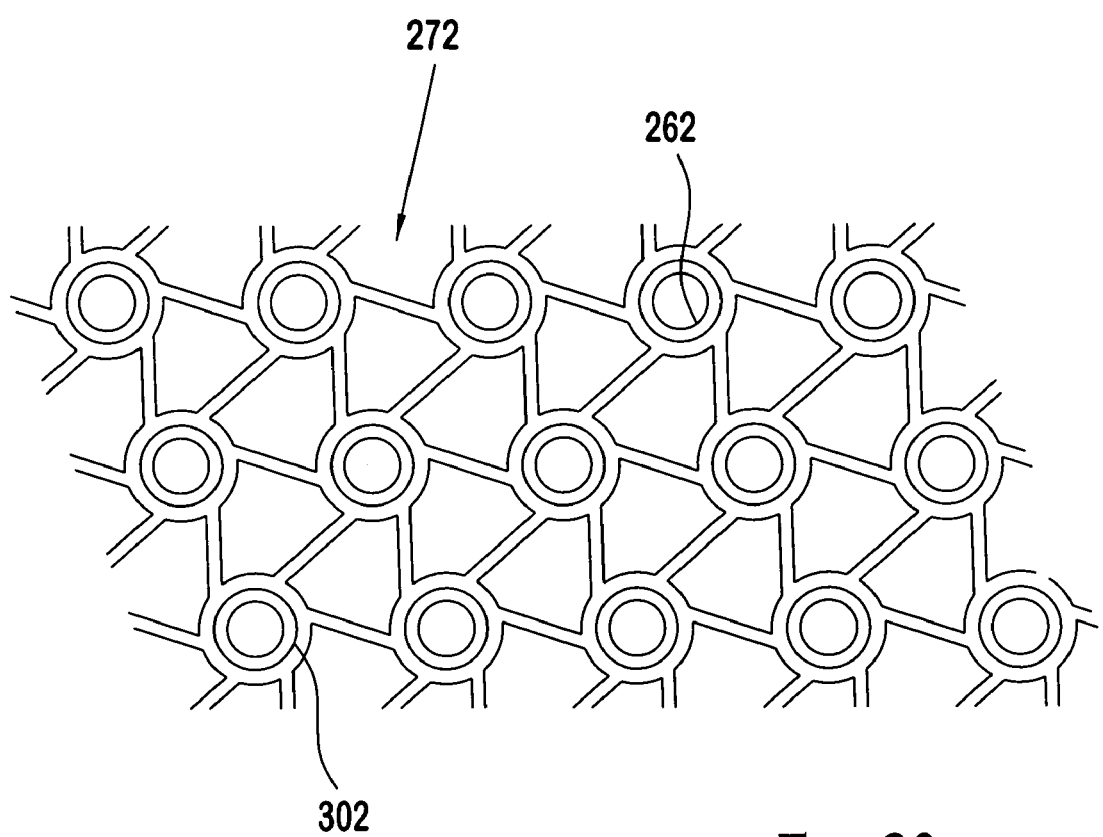
FIG. 30 is an enlarged illustration of the mesh portions of the implants of FIGS. 28 and 29.

Referring to FIG. 30, it will be seen that through-holes 262 may be provided in mesh portions 262, such through-holes preferably being surrounded by rim collars 302 comparable in thickness to a plate portion 274. The through-holes 262 preferably are countersunk to receive mounting screws.

In an alternative embodiment, the maskant layers 192, 196 may be exposed to a movable laser beam which is moved in accordance with a path governed by a CAD data file, wherein the beam removes unwanted maskant. After the laser removes the maskant, the sheet 180 is exposed to heat and/or ultraviolet light to cure and harden the remaining maskant.

The mesh portions 272 preferably are of a thickness of about 0.5 mm and are readily flexed to follow the curvature of a bone.

There is thus provided an improved method for making an article such as a mesh-and-plate surgical implant including both bendable perforated mesh portions and relatively rigid plate portions, wherein the bendable or comfortable perforated portions are integral with and kinematically related to the rigid plate portions. The improved method further provides through-holes for receiving mounting screws during implantation.

The performance of tissue implants may be enhanced by textured surface having undercut characteristics and/or mesh-and-plate characteristics. For example, where a textured surface is specified to promote osseointegration an undercut texture may be specified. Alternatively, where there is need to join the implant with a mechanical securement (e.g., a screw or bolt), the mesh-and-plate texture may be specified. It should be recognized that combining one or more of such textures on a single implant is a viable alternative within the scope of this invention.

Figure 31:
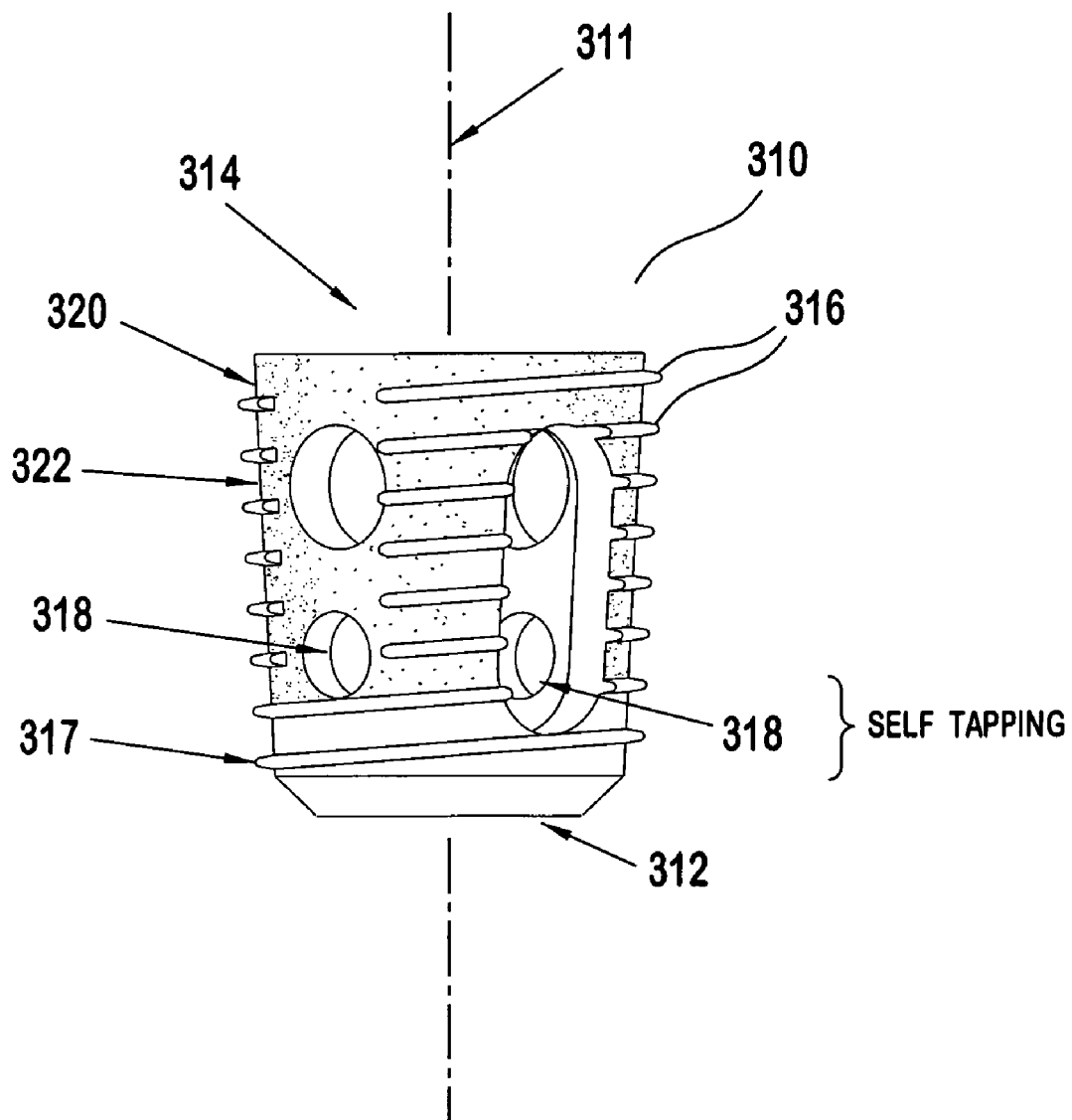
FIG. 31 is a three-dimensional illustration of a textured implant.

FIG. 31 illustrates tissue implant 310, constructed from a bio-compatible material such as metal, glass, plastic, and ceramic. In one preferred embodiment, the bio-compatible material is chemically pure (CP) titanium. Implant 310 is useful in any application in which a secure attachment to an object is desired and would be enhanced by using a textured surface such as discussed herein. Though dental applications and spinal applications have different mechanical objectives, the present invention is useful in both applications. Spinal devices, for example, preferably separate vertebrae in permanent alignment and transfer compressive forces between adjacent vertebrae. Bone ingrowth secures these devices into place, especially with the object of resisting forces that would tend to dislodge them. Dental devices, for example, are preferably screwed into a hole bored in the mandible, whereupon bone ingrowth locks them into place so that teeth or other appliances can be affixed to them. In this application, dental devices must resist tensile and compressive forces and transfer those forces to the bone sufficiently that the bone-to-appliance bond strength is not exceeded.

For example, implant 310 is useful for implantation and/or attachment to hard tissue such as bone in spinal and dental applications and soft tissue. In one embodiment, implant 310 may be adapted for use in a commercial spinal fusion device. Another embodiment of implant 310 may be adapted for use in dental applications, such as with a dental implant in tissue. In one embodiment, implant 310 is particularly well suited as a dental implant post onto which prosthetic teeth or other appliances may be attached.

Implant 310 has a longitudinal axis 311. Distal end 312 of implant 310 typically is inserted into tissue such as a bone (e.g., a jaw bone). In one embodiment, proximal end 314 may be adapted to receive a prosthesis such as an artificial tooth or other dental appliance.

Figure 32:
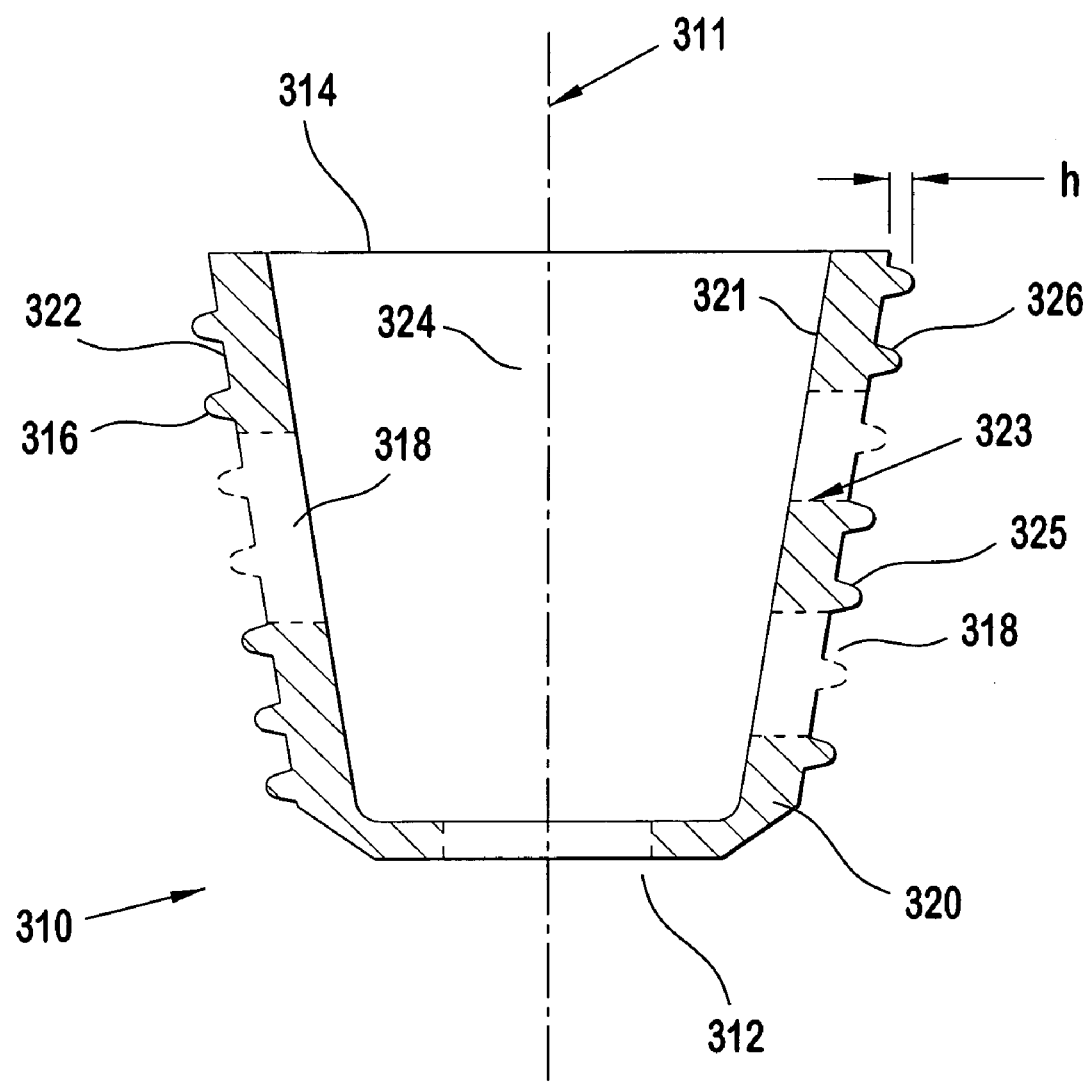
FIG. 32 is a diagrammatic cross-section of an implant.

As shown in FIG. 32, in one embodiment, implant 310 preferably has a wall 320 that is disposed about longitudinal axis 311. In one embodiment, wall 320 is radially disposed about axis 311, and wall 320 has an outer face 322, and an inner face 321. In one embodiment, one or both of outer face 322 and inner face 321 may be substantially parallel to axis 311. In a preferred embodiment, wall 320 is tapered such that distal end 312 of wall 320 has a smaller diameter about axis 311 than at proximal end 314 of wall 320. In one embodiment, wall 320 defines cavity 324.

It was known to use perforations in tissue implants to promote tissue inter-growth necessary to lock an implant to tissue, and to use perforations in tissue implants to vent heat and tissue during installation, as set forth in U.S. Pat. No. 4,960,381, the entire contents of which are incorporated herein by reference. In an embodiment of the present invention, the textured surfaces described below are believed to satisfy one or both of those functions and implant 310 does not include any perforations in wall 320.

In other embodiments, as shown in FIGS. 31, 35, 37A, 37B, and 37C, wall 320 includes one or more apertures 318 which permit the transmission of fluids (e.g., blood), tissue, and tissue fragments (e.g., bone fragments) into cavity 324 to promote, for example, tissue inter-growth (i.e., osseointegration) and/or a heat and/or tissue venting. Aperture 318 may be formed by any method including the methods described herein or other mechanical methods (e.g., drilling), chemical methods (e.g., chemical etching), and/or heat methods (e.g., laser). In one embodiment, apertures 318 are formed by chemical etching of one or both of outer surface 322. Apertures 318 may be more specifically formed by a chemical etching process applied to outer surface 322. In another embodiment, aperture 318 is formed by laser ablation and chemical etching process applied to both outer surface 322 and inner surface 321 such as the method used to create countersinks, mesh geometries and textures as described in U.S. patent application Ser. No. 09/976,722 to Amrich et al., and Ser. No. 10/021,616 to Amrich; the entirety of each being incorporated herein by reference.

As shown in FIGS. 31 and 32, in preferred embodiments, there is at least one aperture 318 that is defined by aperture surface 323, extending between inner face 321 and outer surface 322. Aperture surface 323 may be of any geometry. In one embodiment, aperture surface 323 is substantially flat (e.g., is substantially in a two dimensional plane). In another embodiment, aperture surface 323 is curved such as concave, convex or a compound curve (e.g., a curve with both a concave and a convex component, and multiple concave or convex curves of varying radii and combinations thereof). In one embodiment, aperture surface 323 is disposed normal to axis 311. In another embodiment, aperture surface 323 is oblique to axis 311. Where aperture surface 323 is oblique to axis 311, that angle may be either acute or obtuse. Aperture surface 323 may also be disposed at varying angles to inner face 321 and outer surface 322.

Figure 35:
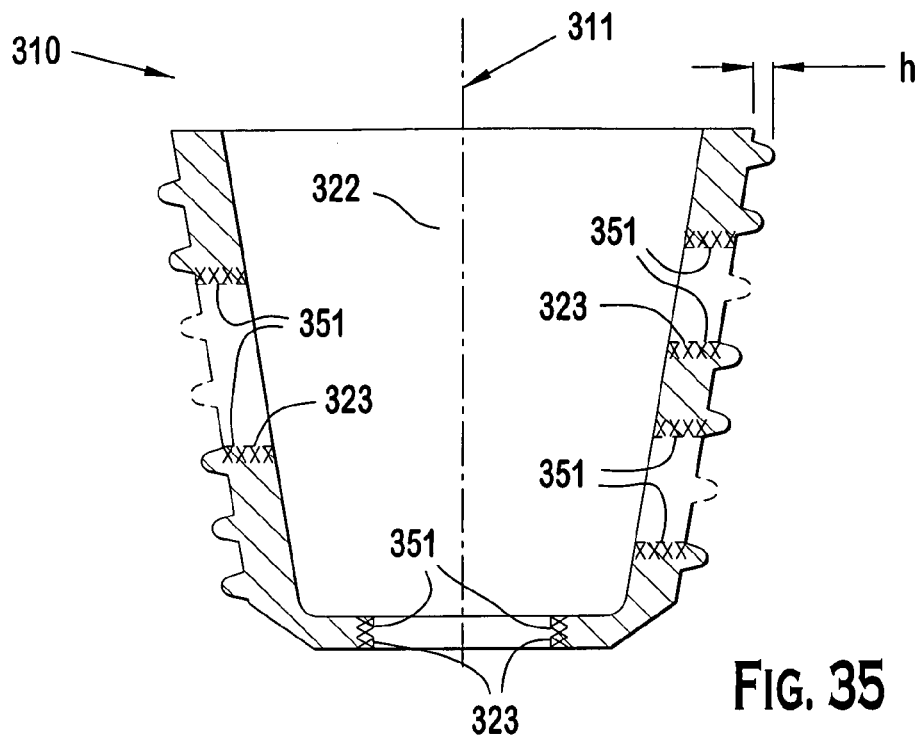
FIG. 35 is a diagrammatic cross sectional view of a textured implant.

In a preferred embodiment, aperture surface 323 is at least partially a textured surface 351 as illustrated in FIG. 35 and as disclosed herein. In one embodiment, the textured surface 351 of aperture surface 323 has a texture that is characterized by undercut recesses such as is created from the methods described herein.

Figure 37A:
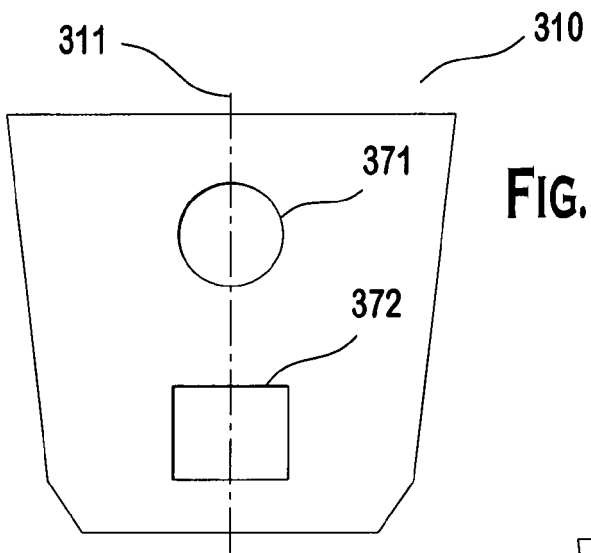
FIGS. 37A–37C illustrate implants with apertures.
Figure 37B:
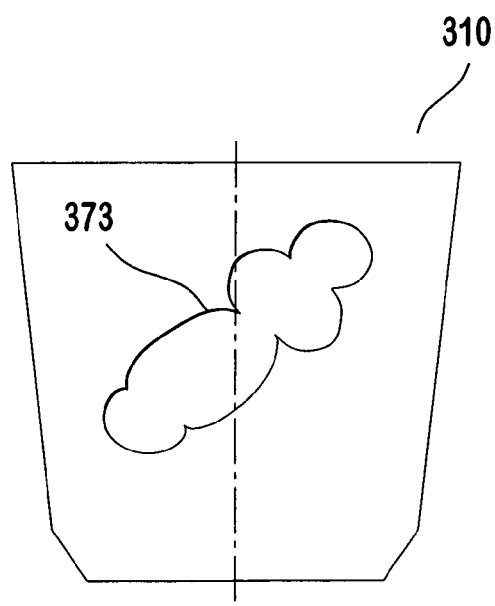
Figure 37C:
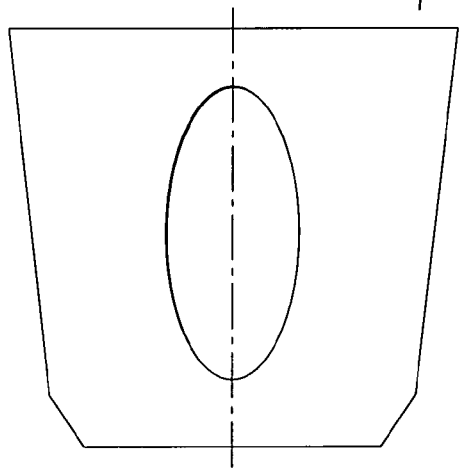

Aperture 318 may be of varying sizes depending on their intended function. Aperture 318 can have any shape including curved (e.g., round aperture 371), angular (e.g., square aperture 372 and triangular (not shown)), complex geometric shapes (e.g., multi-curved aperture 373) and combinations thereof within any one aperture 318 or among different apertures 318 of the same implant 310 (as illustrated in FIG. 37A). In a preferred embodiment, aperture 318 has an oblong geometry with the major axis of aperture 318 longitudinally oriented and the minor axis transversely oriented to axis 311 as illustrated in FIG. 37C. Implant 310 may have one or more aperture 318. In one embodiment, where more than one aperture is included, apertures 318 are either angularly disposed to one another (e.g., less than 180° apart along face 321), longitudinally disposed (e.g., aligned along the longitudinal axis), disposed across from one another (e.g., at 180° relative to face 321), and in geometric combinations thereof. Apertures 318 may extend into the self-tapping region (discussed below) of implant 310.

Figure 36:
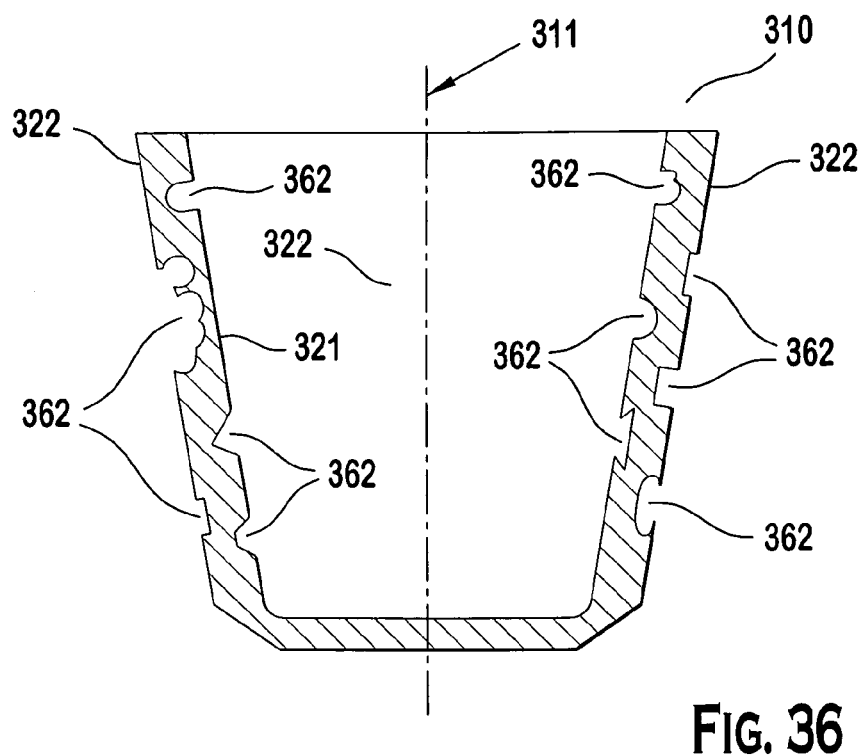
FIG. 36 is a diagrammatic cross sectional view of an implant with recesses.

In one embodiment, as shown in FIG. 36, one or both of outer wall 322 and inner wall 321 include one or more recesses 362 that do not extend through wall 320. Recesses 362 may be formed by any method as described with respect to aperture 318 and may include any attribute of size, shape, and/or configuration discussed with respect to aperture 318. Furthermore, any portion or all of recess 362 may include a texture surface as described.

Figure 38A:
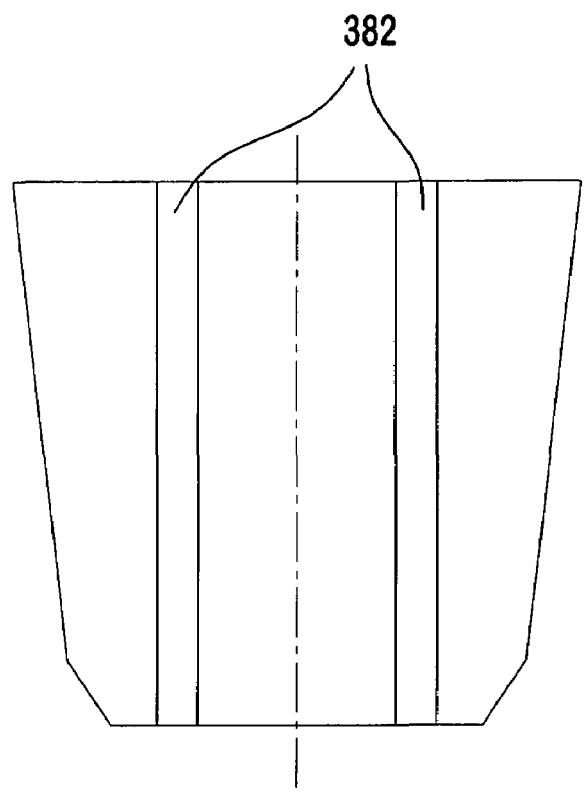
FIGS. 38A–38D illustrate implants with ribs.
Figure 38B:
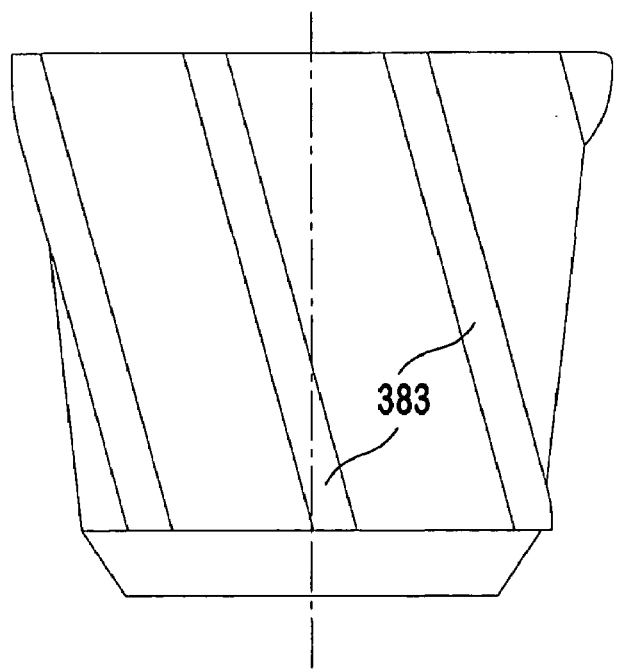
Figure 38C:
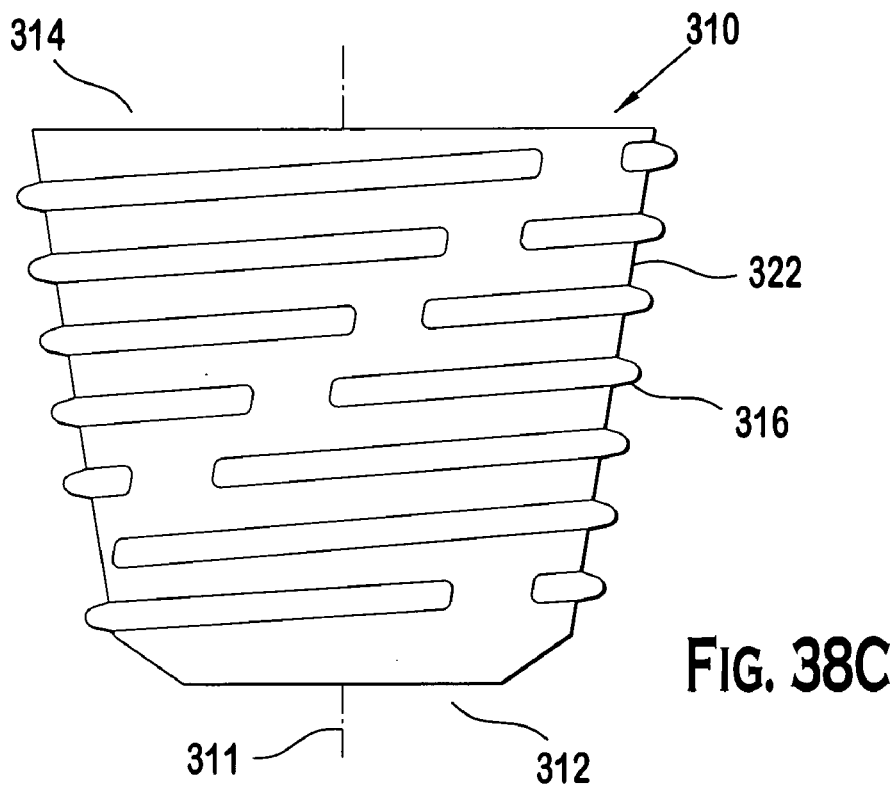

As shown in FIGS. 31, 32, 33, 34, 35, 38A, 38B, 39A, 39B, 39C, 38C, and 38D, in preferred embodiments, implant 310 may also include one or more protrusions 325 from outer face 322. In one embodiment, protrusions 325 may be one or more ribs 326. In one embodiment, ribs 326 may be helically disposed about longitudinal axis 311 to form threads 316 as illustrated in FIG. 31. An implant 310, having threads 316 may typically be installed by screwing implant 310 into tissue (e.g., bone). In one embodiment, thread 316 is continuous from a point approximately at distal end 312 to a point approximately at proximal end 314. In another embodiment, threads 316 may be discontinuous. Where thread 316 is discontinuous, the discontinuity may be at a location proximate to aperture 318 as illustrated in FIG. 31, or the discontinuity may be located where there is no aperture as illustrated in FIG. 38C.

Figure 33:
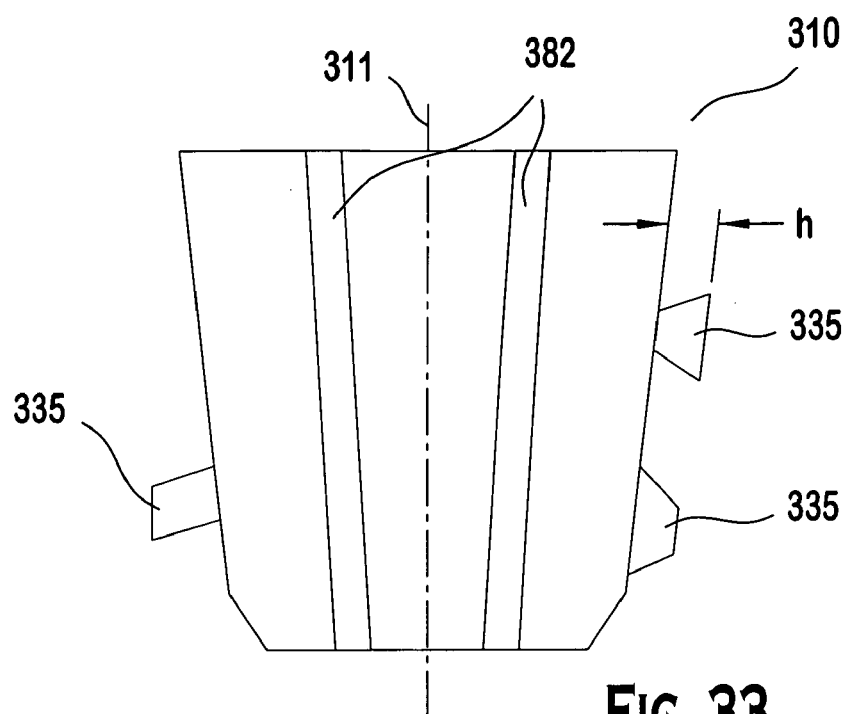
FIG. 33 is an illustration of an implant with protrusions.
Figure 38D:
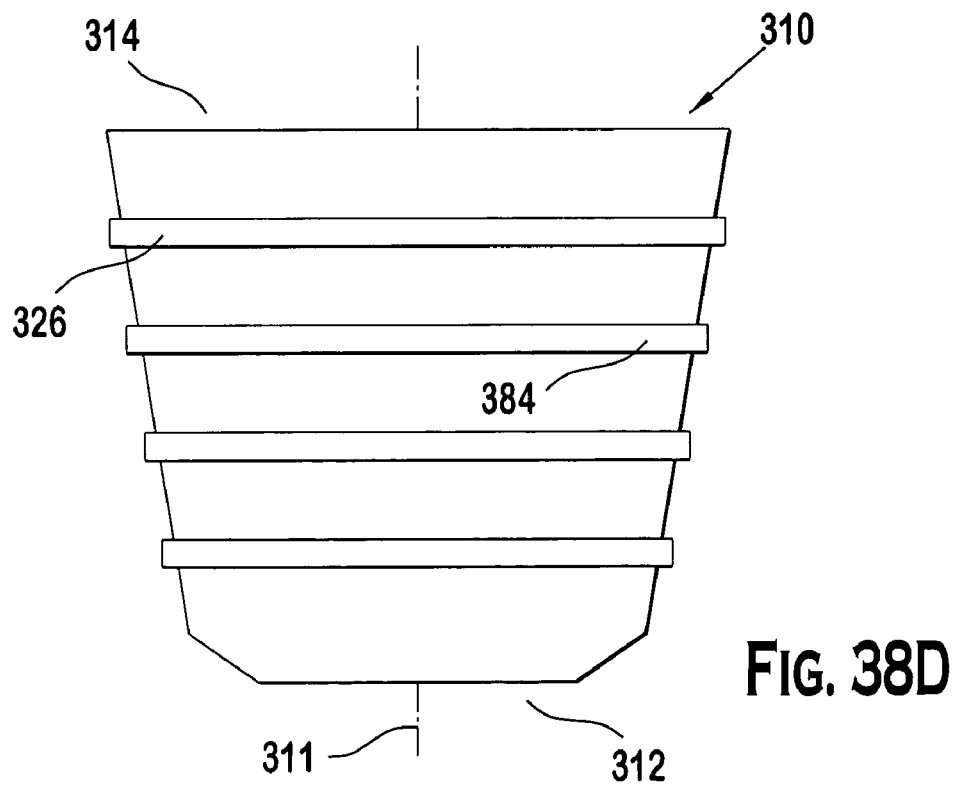

In one embodiment, protrusions 325 are in the form of longitudinal ribs 382 (as illustrated in FIG. 38A and 33) longitudinally disposed on implant 310 such that ribs 382 run generally between proximal end 314 and distal end 312. In one embodiment ribs 382 run generally parallel to axis 311. In another embodiment, angular ribs 383 may be disposed at an angle relative to axis 311, as illustrated in FIG. 38B. In another embodiment, transverse ribs 384 are disposed to form substantially concentric rings that are radially disposed about axis 311 as illustrated in FIG. 38D. Transverse ribs 384 can have any desired pitch angle. In one embodiment, transverse ribs 384 have a low pitch angle. In another embodiment, transverse ribs 384 have a pitch angle of substantially 0°. While longitudinal ribs 382, angular ribs 383, and transverse ribs 384 are shown to be substantially continuous from distal end 312 to proximal end 314, such ribs having discontinuities are also within the scope of the present invention. In one embodiment, ribs 326 may be in the form of discrete segments 335 protruding from wall 320. In one embodiment, discrete segments 335 are evenly distributed about axis 311. In one embodiment evenly spaced discrete segments 335 are of substantially uniform size. In another embodiment, discrete segments 335 are of varying sizes. In another embodiment, discrete segments are unevenly spaced.

Figure 34:
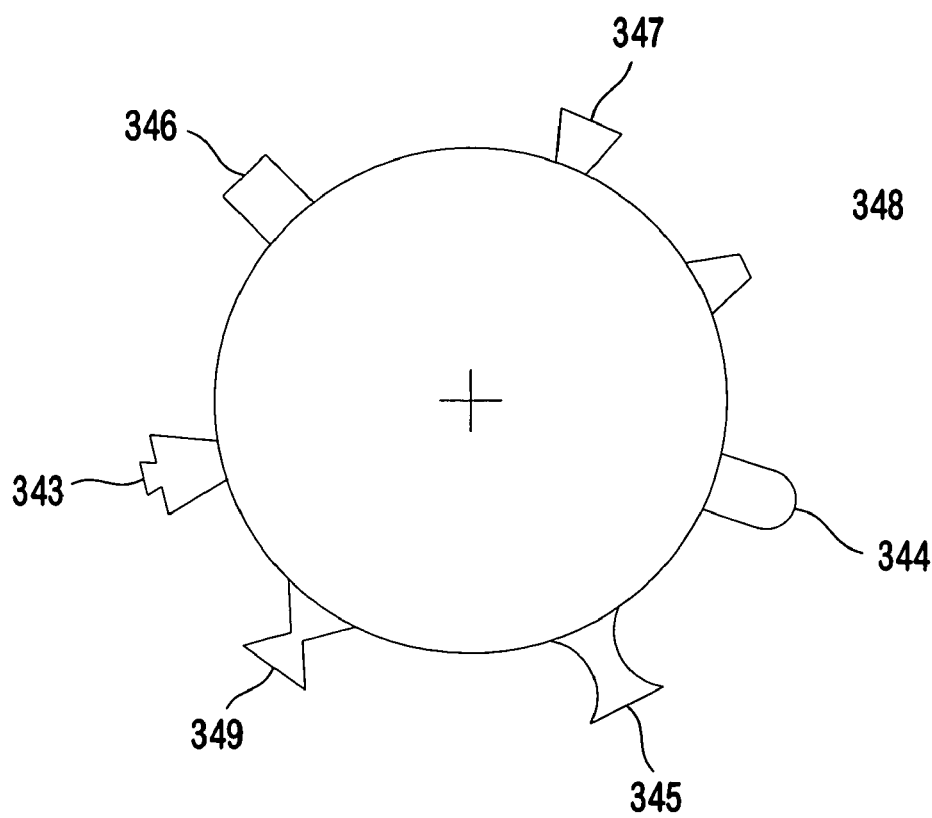
FIG. 34 is a diagrammatic cross-sectional view of an implant with protrusions.

Ribs 326 may have any cross sectional geometry including v-shaped, keystone shaped (e.g., rib 343), curved (e.g., rib 344), trapezoidal with an exterior short face (e.g., rib 348), trapezoidal with an exterior long face (e.g., rib 347), undercut (e.g., rib 345), hourglass (e.g., rib 349) and square (e.g., rib 346), as shown in FIG. 34. In one embodiment, ribs 326 on implant 310 are in the form of longitudinal ribs T32 having one or more of several geometries as shown in FIGS. 32, 33, 34.

It may be necessary, in some procedures, to drill at least one pilot hole or successively larger pilot holes to accommodate implant 310 prior to screwing implant 310 into the tissue. In another embodiment, it may be desirable to drill a large-enough hole where implant 310 can be tapped into place with a mallet. Typically, for implant 310, those embodiments having non-helical ribs are suited for tapping in place while those embodiments including threaded ribs are suited for screwing in place.

In a preferred embodiment, implant 310 may be configured to include a self-tapping thread 317 that is helically disposed about longitudinal axis 311, as shown in FIG. 31. Where self-tapping threads 317 are employed, installation may be accomplished with no pilot hole or with smaller diameter pilot holes than if the self-tapping thread 317 was not included. Self-tapping threads 317 of a preferred embodiment, has a thinner web thickness and more root dimension than crest spacing. The ribs may therefore, appear to be more widely spaced apart. Where self-tapping threads are used, sufficient anchoring can be achieved while reducing the amount of material (e.g., tissue) that is cut or displaced. The tapping force requirement to install a device with the self-tapping features is lower than is necessary for non self-tapping threads.

In one embodiment, threads T13 on implant 310 include one or more portions that are non self-tapping threads. For example, in one embodiment, only a distal portion of the threaded area of implant 310 is self-tapping.

As shown in a preferred embodiment of FIG. 32, protrusions according to the present invention, have a height, h, suitable to restrict removal of implant 310, for example, by the application of axial, longitudinal, and/or radial force.

In one embodiment, outer face 322 and ribs 326 are textured over substantially their entire surface. In another embodiment, outer surface 322 and ribs 326 have textured portions and portions that are relatively smooth (e.g., not textured). More particularly, where a portion of ribs 326 are relatively smooth, that portion may be the crests 392 of ribs 326 as shown in FIG. 39A. In another embodiment, as illustrated in FIG. 39A, outer face 322 is at least partially textured, and ribs 326 are non-textured. Leaving crests 392 without texture is believed to facilitate the installation of implant 310, for example, by avoiding excessive fragmentation to tissue (e.g., bone) surrounding the distal end of implant 310. In a preferred embodiment, outer surface 322 is textured and ribs 326 are not textured. In other embodiments regions of texturing and non-texturing may be used on inner face 321, outer surface 322, aperture surface 323, and ribs 326. In one embodiment, inner face 321 is textured as illustrated in FIG. 39B. In another embodiment, inner face 321 is textured and there are alternating regions of outer surface 322 that are textured as illustrated in FIG. 39C.

Known devices, incorporate an anti-rotation fixture (which may include a hollow cross-drilled structure) that locks the screw device into permanent immobility when bone ingrows the fixtures Such a structure may further serve as a vent during installation. In one embodiment of the present invention, the locking mechanism is integral to the surface of a portion of the threads thus eliminating the need for an additional anti-rotation fixture. In Niznick (U.S. Pat. No. 5,571,017), for example, an anti-rotation fixture characterizes approximately one-third of the device.

In one embodiment, a textured surface may be described as having a higher fractal dimension than a non-textured surface. Depending on the nature of the implant, the fractal dimension may be specified based upon the nature of the implant. For example, where the scratch-fit properties of the implant (e.g., as described above) is of primary importance, a greater fractal dimension may be specified to improve the tissue harvest during implantation. Alternatively, where strength of the bond created by the thread alone is of primary importance, a lower fractal dimension may be specified to limit the disruption of host tissue during implantation. Furthermore, single implant may have regions of varying fractal dimensions that may be dictated by the function of each region on the implant. In a preferred embodiment, a distal region of the implant, that anchors the implant in a tissue, has a lower fractal dimension than a more proximal region that is designed with a preference toward the promotion of tissue growth over short term strength. In another embodiment, regions of higher and lower fractal dimension may alternate along the longitudinal axis 311.

Where a textured component on implant 310 is designed to promote a scratch-fit with tissue that accepts implant 310, the scratch-fit is believed to promote faster healing time by, for example, auto-grafting the patient's bone into the interstices of the surface geometry and causing less compressive trauma to the bone. In one embodiment, the interference fit of the appliance 310 into the prepared site causes the patient's bone B to be shaved by the sharp edges of the surface texture. Since the bone matter is "donated" by the patient, the resulting autograft allows faster healing than is possible with bone matter provided by bone bank donors. The bone matter in one embodiment, originates from the patient and does not need to be denatured, or otherwise have its vitality compromised. In a further embodiment, the bone matter is instantly used as a growth lattice with no local immune reactions. The bone matter may thus be regarded as "alive". Even where a textured surface does not scratch the tissue, it provides a bedding upon which tissue fragments may accumulate and seed. In a preferred embodiment, the elliptical cavities of the textured surface becomes filled with the shavings from the patient's bone without compromising the vitality of shavings and thus not requiring a denaturing step. This bone matter is, therefore, instantly available for growth lattice without local immune reactions. In addition to promoting faster healing times, the higher fractal dimension of the textured surface (relative to a non-textured surface) is believed to ensure a higher shear strength of the bond between the implant and the host tissue. During installation of a preferred embodiment, where ribs 393 are not textured and surface 322 is textured, ribs 393 are believed to initially retain the implant. Where implant 310 is tapered about axis 311, once implant 310 is seated (e.g., pressed or driven to its intended installation depth, or to the depth of the preliminary reaming or drilling), the taper promotes harvesting of bone into the textured surface. In one embodiment, as the device is rotated (e.g., screwed into the host bone), the widening shape generates radial forces that act as a progressively tightening fit.

One may evaluate the benefits gained from implementing these preferred embodiments by observing the correlation between the fractal information dimension and the "pin pushout strength" of a textured body. "Pin pushout strength" refers to a test where candidate textures are applied to small metal dowels. Holes are bored into femur bone in a test subject (canine), and the test sample dowels are pressed into the bores, using a fixture to assure straight and uniform placement. After sufficient time is allowed for healing and bone growth, the bone is removed by pressing the dowel with a pin. The amount of force required to press out the dowel with the pin is measured and recorded by an Instron® tester or similar apparatus. This measures the shear strength of the bone-to-implant bond. Of the samples tested, those embodying the present invention did not fail at the bond line, but rather at some distance outward from the bond line into the vital bone. This result demonstrates that the strength of the implant-to-bone bond was greater than the strength of the host bone itself. In general terms, the greater the fractal information dimension the greater the pin pushout strength which is a quantifiable measurement of bond between a prosthetic body and the tissue to which it is attached.

Tests were performed to compare some embodiments of the present textured surfaces with those of known textured surfaces. The tests include quantifying the degree of roughness attributable to these competing embodiments and comparing that roughness to the effectiveness of an implant bonded with the embodied textured surfaces. The degree of roughness was quantified using the fractal analysis program BENOIT v.1.3, (developed by Trusoft International, Inc. of St. Petersburg, Fla.).

In the study of natural biological growth and many other applications of fractal analysis, it is often appropriate to employ a variation of the "Box Dimension Method" where not only the number of boxes penetrated by the pattern are counted, but where the degree of penetration, or extent of box contents, is weighted in the calculation. This modified method is called the "Information Dimension Method." Both the Box Dimension Method and the Information Dimension Method are described in the literature accompanying the BENOIT software, which is incorporated by reference in its entirety herein.

The simplest method of measuring the fractal dimension of a surface is to photograph a cross section of the prepared surface, and render the outline as a simple white line on a black background in an image stored as a bitmap (BMP) file for processing by the program. If such a line is superimposed on a grid, and the number of boxes penetrated by the line is counted, and repeated at successively smaller box sizes, then plotted in log-log axes, a scale-independent number is reached.

As described in Benoit's software, the box dimension is defined as the exponent Db in the relationship:

$$N(d) \sim 1/d^{Db} \quad \text{Eq.(1a)}$$

where N(d) is the number of boxes of linear size, d, necessary to cover a data set of points distributed in a two-dimensional plane. The basis of this method is that, for objects that are Euclidean, Eq. (1a) defines their dimension. One needs a number of boxes proportional to 1/d to cover a set of points lying on a smooth line, proportional to $1/d^2$ to cover a set of points evenly distributed on a plane, and so on.

This dimension is sometime called grid dimension because for mathematical convenience the boxes are usually part of a grid. One could define a box dimension where boxes are placed at any position and orientation, to minimize the number of boxes needed to cover the set. It is obviously a very difficult computational problem to find, among all the possible ways to cover the set with boxes of size d, the configuration that minimizes N(d). Also, if the overestimation of N(d) in a grid dimension is not a function of scale (i.e., we overestimate N(d) by, say, 5% at all box sizes d), which is a plausible conjecture if the set is self-similar, then using boxes in a grid or minimizing N(d) by letting the boxes take any position is bound to give the same result. This is because a power law such as Eq. (1a) is such that the exponent does not vary if we multiply N(d) or d by any constant.

In practice, to measure Db, one counts the number of boxes of linear size d necessary to cover the set for a range of values of d; and plot the logarithm of N(d) on the vertical axis versus the logarithm of d on the horizontal axis. If the set is indeed fractal, according to BENOIT, this plot will follow a straight line with a negative slope that equals minus Db. To obtain points that are evenly spaced in log-log space, it is best to choose box sizes d that follow a geometric progression (e.g., d=1, 2, 4, 8, . . . ), rather than use an arithmetic progression (e.g., d=1, 2, 3, 4, . . . ).

A choice to be made in this procedure is the range of values of d. Trivial results are expected for very small and very large values of d. A conservative choice may be to use as the smallest d ten times the smallest distance between points in the set, and as the largest d the maximum distance between points in the set divided by ten. Alternatively, one may exceed these limits and discard the extremes of the log-log plot where the slope tends to zero.

In theory, for each box size, the grid should be overlaid in such a way that the minimum number of boxes is occupied. This is accomplished in Benoit by rotating the grid for each box size through 90 degrees and plotting the minimum value of N(d). Benoit permits the user to select the angular increments of rotation.

In the study of natural biological growth and many other applications of fractal analysis, it is often more appropriate to employ a variation of the Box Dimension method where not only the number of boxes penetrated by the pattern are counted, but where the degree of penetration, or extent of box contents is weighted in the calculation. This is the Information Dimension Method.

The Information Dimension is often encountered in physics literature, and is generally different from the box dimension. In the definition of box dimension, a box is counted as occupied and enters the calculation of N(d) regardless of whether it contains one point or a relatively large number of points. The information dimension effectively assign weights to the boxes in such a way that boxes containing a greater number of points count more than boxes with less points.

The information entropy I(d) for a set of N(d) boxes of linear size d is defined as $$I(d) = -\sum_{i=1}^{N(d)} m_i \log(m_i) \quad \text{Eq. (1b)}$$

where $m_1$ is:

$$m_i = \frac{Mi}{M} \quad \text{Eq. (2)}$$

where $M_i$ is the number of points in the i-th box and m is the total number of points in the set.

Consider a set of points evenly distributed on the two-dimensional plane. In this case, we will have $$N(d) \approx \frac{1}{d^2} \qquad \text{Eq. (3)}$$
$$m_i \approx d^2$$

so that Eq. (2) can we written as:

$$\text{Eq. (4):} \quad I(d) \approx -N(d)[d^2 \log(d^2)] \approx -\frac{1}{d^2}[2d^2 \log(d)] = -2\log(d)$$

For a set of points composing a smooth line we would find:

$$I(d) \approx -\log(d)$$

Therefore, we can define the information dimension $D_i$ as in $$I(d) \approx D_1 \log(d) \qquad \text{Eq. (5)}$$

In practice, to measure $D_i$ one covers the set with boxes of linear size d keeping track of the mass $m_i$ in each box, and calculates the information entropy I(d) from the summation in [Eq. (1b)]. If the set is fractal, a plot of I(d) versus the logarithm of d will follow a straight line with a negative slope equal to $-D_i$.

It was noted above that the information dimension differs from the box dimension in that it weighs more heavily boxes containing more points. To see this, let us write the number of occupied boxes N(d) and the information entropy I(d), in terms of the masses $m_i$, contained in each box:

$$N(d) = \sum_i m_i^o; \quad I(d) = -\sum_i m_i \log(m_i) \qquad \text{Eq. (6)}$$

The first expression in Eq. (6) is a somewhat elaborate way to write N(d), but it shows that each box counts for one, if $m_i > 0$. The second expression is taken directly from the definition of the information entropy Eq. (1b). The number of occupied boxes, N(d), and the information entropy I(d) enter on different ways into the calculation of the respective dimensions, it is clear from [Eq. (6)] that:

$$D_6 \leq D_i \qquad \text{Eq. (7)}$$

The condition of equality between the dimensions [Eq. (7)] is realized only if the data set is uniformly distributed on a plane.

The following table illustrates the relationship between the Information Dimension of certain textural products and the Pin Pushout strength for selected products. Also illustrated in the following table is the standard deviation of the Information Dimension as calculated by the Benoit software. Higher standard deviations number are illustrative of a more "random", less ordered surface texture.

TABLE 1

| Textured Surface Image | Information Dimension | Standard Deviation | Pin Pushout, kN($^2$) |
|---|---|---|---|
| Zirconium Tecotex ® Samp. 1 | 1.91496 | 0.0002102 | 2.83 |
| Zirconium Tecotex ® Samp. 2 | 1.93619 | 0.0002025 | |
| Zirconium Tecotex ® Samp. 3 | 1.90834 | 0.0001329 | |
| Titanium Tecotex ® | 1.906 | 0.00011 | |
| Stainless Tecotex ® | 1.9329 | 0.00011 | |
| Cycam 555 surface | 1.77720 | 0.0036506 | 1.56 |
| Cycam555, Sample 2 | 1.69434 | 0.0015109 | |
| Sintered Spheres | 1.9236 | 0.000022 | 2.67 |
| CrCo Tecotex ® | 1.86023 | 0.00000 | |

In any of the above embodiments, one or more of the elements described may be included in implant 310. For example, textured portion 351 has any desired texture depending on the particular use of implant 310. For example, textured portions 351 may include patterns formed from the methods described herein. Textured portions may also include random patterns as described in U.S. Pat. No. 5,258,098, U.S. Pat. No. 5,507,815, U.S. Pat. No. 5,922,029, and U.S. Pat. No. 6,193,762 each issued to Wagner et al., the entire contents of which are hereby incorporated by reference. The textures may also include the patterns described in U.S. Pat. No. 5,975,903 issued to Shoher et al., U.S. Pat. No. 6,095,817 issued to Wagner et al., U.S. Pat. No. 6,217,333 B1 issued to Ercoli, U.S. Pat. No. 5,571,017 issued to Niznick, U.S. Pat. No. 5,639,237 issued to Fontenot, and U.S. Pat. No. 4,960,381 issued to Niznick the entire contents of which are hereby incorporated by reference.

Although the foregoing description is directed to the preferred embodiments of the invention, it is noted that many additional changes, variations and modifications in the details, materials, steps and arrangement of parts, which have been herein described and illustrated in order to explain the nature of the invention, will be apparent to those skilled in the art, and may be made without departing from the spirit or scope of the invention.

All references referred to herein are hereby incorporated by reference in their entirety.

We claim:

1. A prosthetic device comprising:
   a selected repeatable pattern having
      a surface defining a cavity having a geometry characterized by at least one complex ellipsoid, and
      an undercut face projecting over a portion of the cavity.

2. The prosthetic device of claim 1 having an outer surface and a rib outwardly protruding from the outer surface.

3. The prosthetic device of claim 2 wherein the rib comprises a cross sectional geometry taken from the group consisting of v-shaped, keystone, curved, trapezoidal, undercut, hourglass, and square.

4. The prosthetic device of claim 2 wherein the rib comprises a rib surface that is substantially smooth.

5. The prosthetic device of claim 2 further comprising:
   a longitudinal axis,
   a wall, disposed about the longitudinal axis, characterized by an inner surface and the outer surface, and
   an aperture extending from the inner surface to the outer surface.

6. The prosthetic device of claim 2 wherein the rib is a thread.

7. The prosthetic device of claim 6 wherein the thread is a self-taping thread.

8. The prosthetic device of claim 6 comprising a first end and a second end, the thread extending from proximate the first end to proximate the second end.

9. The prosthetic device of claim 6 wherein the thread is continuous.

10. The prosthetic device of claim 6 wherein the thread is segmented.

11. The prosthetic device of claim 1 further comprising a longitudinal axis, and a plurality of ribs outwardly projecting from the outer surface, the ribs being radially disposed about the longitudinal axis.

12. The prosthetic device of claim 11 wherein the ribs are substantially parallel to each other.

13. The prosthetic device of claim 11 wherein the ribs are longitudinally disposed on the device.

14. The prosthetic device of claim 11 wherein the ribs are disposed on the device oblique to the longitudinal axis.

15. A prosthetic device comprising:
a plurality of cavities recessed into the prosthetic device;
a plurality of curved concave surfaces having a complex ellipsoid shape, each of the plurality of concave surfaces at least partially defining a bottom of one of the plurality of cavities;
the plurality of curved concave surfaces further defining a plurality of projections extending from the bottom of the cavities to form an undercut surface.
wherein the plurality of cavities and the plurality of projections are arranged in a selected repeatable pattern.

16. The prosthetic device of claim 15 wherein the complex ellipsoid is a non-spherical complex ellipsoid.

17. The prosthetic device of claim 15 wherein the plurality of curved concave surfaces are serially aligned to form a repeating pattern.

18. The prosthetic device of claim 17 wherein the repeating pattern is a saw-tooth pattern.

19. The prosthetic device of claim 15 wherein the complex ellipsoid shape is substantially identical for at least two of the curved concave faces.

20. The prosthetic device of claim 15 wherein the complex ellipsoid shape is substantially identical for substantially all of the curved concave faces.

21. The prosthetic device of claim 15 wherein the plurality of projections have a geometry defined by a relationship of at least two complex ellipsoids.

22. The prosthetic device of claim 15 wherein the plurality of projections include a peak coincident with an outer surface of the prosthetic device.

23. The prosthetic device of claim 15 wherein the plurality of projections include a peak located between the bottom and an original outer surface of the prosthetic device.

24. The prosthetic device of claim 15 wherein the plurality of projections include a peak located between the bottom and an original outer surface of the prosthetic device the peak being defined by at least two complex ellipsoids that do not overlap one another.

25. The prosthetic device of claim 15 wherein the plurality of projections include a peak taken from the group consisting of a) coincident with an original outer surface of the prosthetic device, b) located between the bottom and the original outer surface and being defined by at least two overlapping complex ellipsoids, c) located between the bottom and the original outer surface and defined by at least two complex ellipsoids that do not overlap one another, and d) combinations thereof.

* * * * *